United States Patent
Hasegawa et al.

(10) Patent No.: US 10,365,417 B2
(45) Date of Patent: Jul. 30, 2019

(54) NEAR-INFRARED CUT FILTER AND IMAGING DEVICE

(71) Applicant: AGC Inc., Chiyoda-ku (JP)

(72) Inventors: Makoto Hasegawa, Koriyama (JP); Takashi Sugiyama, Koriyama (JP)

(73) Assignee: AGC Inc., Chiyoda-ku (JP)

( * ) Notice: Subject to any disclaimer, the term of this patent is extended or adjusted under 35 U.S.C. 154(b) by 461 days.

(21) Appl. No.: 15/279,700

(22) Filed: Sep. 29, 2016

(65) Prior Publication Data

US 2017/0017024 A1 Jan. 19, 2017

Related U.S. Application Data

(63) Continuation of application No. PCT/JP2016/051021, filed on Jan. 14, 2016.

(30) Foreign Application Priority Data

Jan. 14, 2015 (JP) ................................. 2015-005383
Aug. 20, 2015 (JP) ................................. 2015-163264

(51) Int. Cl.
*C07D 209/08* (2006.01)
*C07D 207/20* (2006.01)
(Continued)

(52) U.S. Cl.
CPC ........... *G02B 5/208* (2013.01); *C07D 207/20* (2013.01); *C07D 209/08* (2013.01); *G02B 5/22* (2013.01); *G02B 5/223* (2013.01); *G02B 5/26* (2013.01)

(58) Field of Classification Search
CPC ........ G02B 5/208; G02B 5/223; G02B 5/281; G02B 5/282; G02B 5/22; G02B 5/26; G02B 1/04; C07D 207/20; C07D 209/08
(Continued)

(56) References Cited

U.S. PATENT DOCUMENTS 4,333,983 A * 6/1982 Allen ................. B29D 11/0073
428/336
5,282,084 A * 1/1994 Hatano .................. G02B 1/116
359/360
(Continued)

FOREIGN PATENT DOCUMENTS

CN 102985856 3/2013
CN 103261927 8/2013
(Continued)

OTHER PUBLICATIONS

Notice of Opposition dated Apr. 20, 2018 in corresponding Japanese Patent Application No. 2016-545370, 5 pages.
(Continued)

*Primary Examiner* — Collin X Beatty
(74) *Attorney, Agent, or Firm* — Oblon, McClelland, Maier & Neustadt, L.L.P.

(57) ABSTRACT

A near-infrared cut filter has an absorption layer and a reflection layer and satisfies following requirements:
average transmittance (R) of 620-750 nm is ≤20%, average transmittance (G) of 495-570 nm is ≥90%, and a ratio (R)/(G) is ≤0.20;
$|T_{0(600-725)}-T_{30(600-725)}|$ is ≤3%·nm where $T_{0(600-725)}$ is a transmittance integral value of 600-725 nm in a spectral transmittance curve (0°), and $T_{30(600-725)}$ is a transmittance integral value of 600-725 nm in a spectral transmittance curve (30°);
wavelengths $\lambda IR_{T(80)}$, $\lambda IR_{T(50)}$, and $\lambda IR_{T(20)}$ where transmittance becomes 80%, 50%, and 20% respectively in 550-750 nm in the spectral transmittance curve (0°) normalized by maximum transmittance in 450-650 nm satisfy following formulae: $0 \leq \lambda IR_{T(80)}-\lambda_{T(80)} \leq 30$ nm, $0 \leq \lambda IR_{T(50)}-\lambda_{T(50)} \leq 35$ nm, and $0 \leq \lambda IR_{T(20)}-\lambda_{T(20)} \leq 37$ nm where $\lambda_{T(80)}$, $\lambda_{T(50)}$, and $\lambda_{T(20)}$ are wavelengths on
(Continued)

a long wavelength side where relative visibility of 0.8, 0.5 and 0.2 is exhibited in a relative visibility curve.

26 Claims, 3 Drawing Sheets

(51) Int. Cl.
*G02B 5/26* (2006.01)
*G02B 5/22* (2006.01)
*G02B 5/20* (2006.01)

(58) Field of Classification Search
USPC .................................. 359/350, 359, 587, 589
See application file for complete search history.

(56) References Cited

U.S. PATENT DOCUMENTS

| | | | |
|---|---|---|---|
| 6,985,170 | B1 | 1/2006 | Tsuyuki |
| 8,159,596 | B2 | 4/2012 | Yamano |
| 2004/0033640 | A1* | 2/2004 | Izumi ................ H01L 27/1462 438/59 |
| 2009/0136730 | A1* | 5/2009 | Nakano .................. C08K 3/38 428/220 |
| 2009/0294634 | A1* | 12/2009 | Kurahashi .............. G03B 11/00 250/208.1 |
| 2012/0145901 | A1* | 6/2012 | Kakiuchi ............... G02B 5/208 250/330 |
| 2012/0243077 | A1* | 9/2012 | Osawa ................. G02B 3/0056 359/356 |
| 2013/0094075 | A1 | 4/2013 | Saitoh et al. |
| 2014/0055652 | A1 | 2/2014 | Hasegawa et al. |
| 2014/0063597 | A1 | 3/2014 | Shimmo et al. |
| 2014/0091419 | A1 | 4/2014 | Hasegawa et al. |
| 2014/0264202 | A1 | 9/2014 | Nagaya et al. |
| 2015/0146057 | A1 | 5/2015 | Konishi et al. |

FOREIGN PATENT DOCUMENTS

| | | |
|---|---|---|
| CN | 104755969 | 7/2015 |
| DE | 100 57 141 A1 | 5/2002 |
| EP | 2 584 385 A1 | 4/2013 |
| JP | 2000-137172 | 5/2000 |
| JP | 2001-42230 | 2/2001 |
| JP | 2006-106570 | 4/2006 |
| JP | 2006-301489 | 11/2006 |
| JP | 2008-51985 | 3/2008 |
| JP | 2008-181028 | 8/2008 |
| JP | 4169545 | 10/2008 |
| JP | 2011-100084 | 5/2011 |
| JP | 2012-103340 | 5/2012 |
| JP | 2012-137645 | 7/2012 |
| JP | 2012-137646 | 7/2012 |
| JP | 2012-137647 | 7/2012 |
| JP | 2012-137648 | 7/2012 |
| JP | 2012-137649 | 7/2012 |
| JP | 2012-137650 | 7/2012 |
| JP | 2012-137651 | 7/2012 |
| JP | 2012-159658 | 8/2012 |
| JP | 5013022 | 8/2012 |
| JP | 2013-68688 A | 4/2013 |
| JP | 2013-190553 | 9/2013 |
| JP | 2014-52482 | 3/2014 |
| JP | 2014-59550 | 4/2014 |
| JP | 2014-63144 A | 4/2014 |
| JP | 2014-66918 A | 4/2014 |
| JP | 2014-126642 | 7/2014 |
| JP | 2014-191346 A | 10/2014 |
| KR | 10-2010-0061371 | 6/2010 |
| KR | 10-2013-0018803 | 2/2013 |
| KR | 10-2015-0046016 | 4/2015 |
| TW | 201224533 A1 | 6/2012 |
| TW | 201245836 A1 | 11/2012 |
| WO | WO 2011/158635 A1 | 12/2011 |
| WO | WO 2012/105343 A1 | 8/2012 |
| WO | WO 2013/054864 A1 | 4/2013 |
| WO | WO 2014/002864 A1 | 1/2014 |
| WO | WO 2014/030628 A1 | 2/2014 |
| WO | WO 2014/088063 A1 | 6/2014 |
| WO | WO 2014/163405 A1 | 10/2014 |
| WO | WO 2014/168189 A1 | 10/2014 |
| WO | WO 2014/192714 A1 | 12/2014 |
| WO | WO 2014/192715 A1 | 12/2014 |
| WO | WO 2015/022892 A1 | 2/2015 |
| WO | WO 2015/034211 A1 | 3/2015 |
| WO | WO 2015/034217 A1 | 3/2015 |
| WO | WO 2015/099060 A1 | 7/2015 |
| WO | WO 2015/122595 A1 | 8/2015 |

OTHER PUBLICATIONS

International Search Report dated Apr. 19, 2016 in PCT/JP2016/051021, filed on Jan. 14, 2016 ( with English Translation.
Written Opinion dated Apr. 19, 2016 in PCT/JP2016/051021, filed on Jan. 14, 2016.

* cited by examiner

NEAR-INFRARED CUT FILTER AND IMAGING DEVICE

CROSS-REFERENCE TO RELATED APPLICATIONS

The present application is a continuation of prior International Application No. PCT/JP2016/051021 filed on Jan. 14, 2016 which is based upon and claims the benefit of priority from Japanese Patent Applications Nos. 2015-005383 filed on Jan. 14, 2015, and 2015-163264 fled on Aug. 20, 2015; the entire contents of all of which are incorporated herein by reference.

FIELD

Embodiments described herein relate generally to a near-infrared cut filter and an imaging device.

BACKGROUND ART

In an imaging device using a solid-state image sensing device of a digital still camera or the like, a near-infrared cut filter transmitting visible light but blocking infrared light is typically disposed in an optical path to the solid-state image sensing device, so as to make the sensitivity of the solid-state image sensing device close to the visibility of human.

As such a near-infrared cut filter, a filter is known in which an absorption layer containing a dye absorbing near-infrared light, and a reflection layer having stacked dielectric thin films with different refractive indexes to reflect and block near-infrared light by interference of light are combined. In this filter, a dielectric multilayer film constituting the reflection layer has optical film thicknesses of respective films which are different depending on an incident angle of light. Thus, there is a problem that it has incident angle dependence in its spectral characteristic, and that color reproducibility is different depending on the incident angle.

On the other hand, Patent Reference 1 (JP-B2 4169545) discloses a filter using a near-infrared absorbing glass in which CuO or the like is added to a fluorophosphate-based glass or a phosphate-based glass so as to enable selective absorption of near-infrared light. However, the incident angle dependence is recognized also in this filter, and the problem of different color reproducibility depending on the incident angle remains unsolved.

Further, Patent Reference 2 (JP-A 2008-051985) discloses a near-infrared cut filter including an absorption layer and a reflection layer constituted of a dielectric multilayer film, the filter having a spectral characteristic to exhibit high transmittance exceeding 90% in a visible wavelength range and exhibit low transmittance of 5% or less in an infrared wavelength range. In this filter, for example, the wavelength at which transmittance becomes 50% is in the vicinity of 650 nm, and the transmittance on a long wavelength side is high with reference to a relative visibility curve, having a problem that color reproducibility particularly of redness cannot be obtained with high accuracy.

Moreover, Patent Reference 3 (JP-A 2014-052482) similarly discloses a near-infrared cut filter including an absorption layer and a reflection layer constituted of a dielectric multilayer film. This filter has a spectral characteristic closer to the relative visibility curve on the long wavelength side than that disclosed in Patent Reference 2. However, the above-described incident angle dependence of the spectral characteristic of this filter is large, and there is still a problem that color reproducibility differs depending on the incident angle.

SUMMARY

As described above, among the conventional near-infrared cut filters, there are few that have the spectral characteristic close to the relative visibility curve particularly on the long wavelength side, and even those having such a spectral characteristic close to the relative visibility curve, there is a problem that there is incident angle dependence in their spectral characteristics. Thus, good color reproducibility cannot be obtained. Therefore, it is an object of the present invention to provide a near-infrared cut filter exhibiting a spectral characteristic close to the relative visibility curve particularly on the long wavelength side, having small incident angle dependence and an excellent oblique-incidence property, and an imaging device using such a filter and having excellent color reproducibility.

A near-infrared cut filter according to one aspect of the present invention has an absorption layer and a reflection layer and satisfies following requirements (1) to (3):
(1) average transmittance (R) in the wavelength range of 620 to 750 nm is 20% or less and average transmittance (G) in the wavelength range of 495 to 570 nm is 90% or more in a spectral transmittance curve at an incident angle of 0°, and the ratio (R)/(G) of the average transmittance is 0.20 or less;
(2) difference $|T_{0(600\text{-}725)} - T_{30(600\text{-}725)}|$ Å between an integral value $T_{0(600\text{-}725)}$ of transmittance in the wavelength range of 600 to 725 nm in the spectral transmittance curve at an incident angle of 0°, and an integral value $T_{30\ (600\text{-}725)}$ of transmittance in the wavelength range of 600 to 725 nm in a spectral transmittance curve at an incident angle of 30° is 3%·nm or less; and
(3) the near-infrared cut filter has a wavelength $\lambda IR_{T(80)}$ at which transmittance becomes 80%, a wavelength $\lambda IR_{T(50)}$ at which transmittance becomes 50%, and a wavelength $\lambda IR_{T(20)}$ at which transmittance becomes 20% in the wavelength range of 550 to 750 nm in the spectral transmittance curve at an incident angle of 0° normalized by maximum transmittance of a wavelength range of 450 to 650 nm, and the wavelengths $\lambda IR_{T(80)}$, $\lambda IR_{T(50)}$, and $\lambda IR_{T(20)}$ satisfy following formulae (a), (b) and (c), respectively:

$$0 \leq \lambda IR_{T(80)} - \lambda_{T(80)} \leq 30 \text{ nm} \quad (a),$$

$$0 \leq \lambda IR_{T(50)} - \lambda_{T(50)} \leq 35 \text{ nm} \quad (b),$$

$$0 \leq \lambda IR_{T(20)} - \lambda_{T(20)} \leq 37 \text{ nm} \quad (c),$$

where $\lambda_{T(80)}$, $\lambda_{T(50)}$ and $\lambda_{T(20)}$ are wavelengths on a long wavelength side where relative visibility of 0.8, 0.5 and 0.2 is exhibited in a relative visibility curve, respectively.

Further, an imaging device according to another aspect of the present invention has the above-described near-infrared cut filter.

According to the present invention, a near-infrared cut filter exhibiting a spectral characteristic close to a relative visibility curve particularly on a long wavelength side and having small incident angle dependence can be obtained, and an imaging device using such a near-infrared cut filter and having excellent color reproducibility can be obtained.

DETAILED DESCRIPTION

An embodiment of the present invention will be described below. A near-infrared cut filter may also be abbreviated as "NIR filter" herein.

<NIR Filter>

The NIR filter of one embodiment of the present invention (hereinafter referred to as the "present filter") has an absorption layer and a reflection layer.

The present filter may have one each of the absorption layer and the reflection layer, or two or more layers of one of them, or two or more layers of both of them. When the filter has two or more layers, each layer may be of the same structure or different structure.

One example is that when the filter has two or more absorption layers, one layer may be a near-infrared absorbing layer constituted of a resin containing a near-infrared absorbing dye as that which will be described later, and the other layer may be an ultraviolet absorbing layer constituted of a resin containing an ultraviolet absorbing dye as that which will be described later.

Further, the present filter may further have a transparent substrate. In this case, the absorption layer and the reflection layer may be provided on the same main surface of the transparent substrate, or may be provided on different main surfaces. When the absorption layer and the reflection layer are provided on the same main surface, the order of stacking them is not particularly limited.

The present filter may further have another functional layer such as an anti-reflection layer.

A structural example of the present filter will be explained below by using drawings.

Figure 1A:
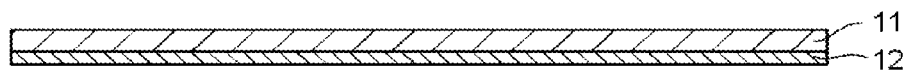
FIG. 1A is a cross-sectional view schematically illustrating an example of an NIR filter according to one embodiment.

FIG. 1A illustrates a structural example having an absorption layer 11 and a reflection layer 12.

Figure 1B:
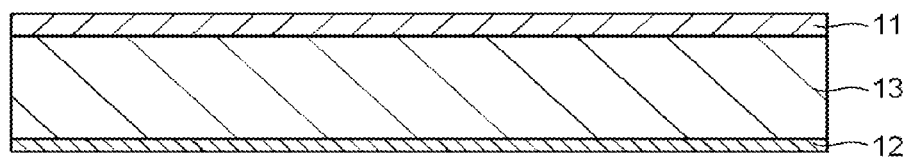
FIG. 1B is a cross-sectional view schematically illustrating another example of the NIR filter according to one embodiment.

FIG. 1B illustrates a structural example having an absorption layer 11 on one main surface of a transparent substrate 13, and a reflection layer 12 on another main surface of the transparent substrate 13.

Note that "having another layer of the absorption layer 11, the reflection layer 12, or the like on one main surface of the transparent substrate 13" is not limited to the case where another layer is provided in contact with the transparent substrate 13, and includes the case where another functional layer is provided between the transparent substrate 13 and the other layer. The same applies to structures below.

In FIGS. 1A and 1B, the absorption layer 11 may include two layers of a near-infrared absorbing layer and an ultraviolet absorbing layer. In FIG. 1A, the structure may have a near-infrared absorbing layer on the reflection layer 12 and an ultraviolet absorbing layer on the near-infrared absorbing layer, or the structure may have an ultraviolet absorbing layer on the reflection layer 12 and a near-infrared absorbing layer on the ultraviolet absorbing layer.

Similarly, in FIG. 1B, the structure may have a near-infrared absorbing layer on the transparent substrate 13 and an ultraviolet absorbing layer on the near-infrared absorbing layer, or the structure may have an ultraviolet absorbing layer on the transparent substrate 13 and a near-infrared absorbing layer on the ultraviolet absorbing layer.

Figure 1C:
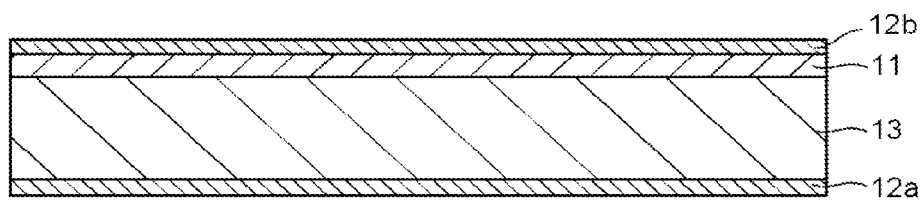
FIG. 1C is a cross-sectional view schematically illustrating another example of the NIR filter according to one embodiment.

FIG. 1C illustrates a structural example having an absorption layer 11 on one main surface of a transparent substrate 13, and having reflection layers 12a and 12b on another main surface thereof and a main surface of the absorption layer 11.

Figure 1D:
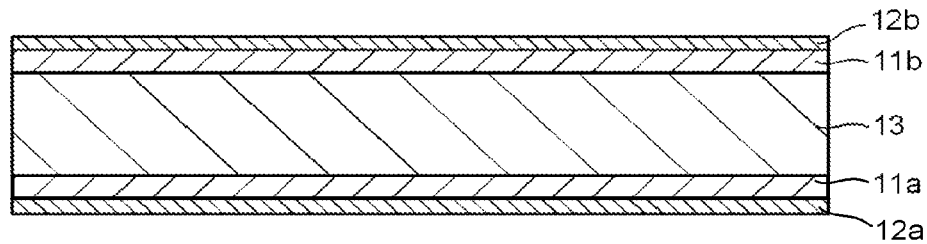
FIG. 1D is a cross-sectional view schematically illustrating another example of the NIR filter according to one embodiment.

FIG. 1D illustrates a structural example having absorption layers 11a and 11b on both main surfaces of the transparent substrate 13, and further having reflection layers 12a and 12b on main surfaces of the absorption layers 11a and 11b.

In FIGS. 1C and 1D, the two layers of reflection layers 12a and 12b to be combined may either be the same or different. For example, the reflection layers 12a and 12b may be structured to have a property to reflect an ultraviolet wavelength range and a near-infrared wavelength range and transmit a visible wavelength range, such that the reflection layer 12a reflects the ultraviolet wavelength range and a first near-infrared wavelength range, and the reflection layer 12b reflects the ultraviolet wavelength range and a second near-infrared wavelength range. Note that in the near-infrared wavelength range, the first near-infrared wavelength range is located on a short wavelength side with respect to the second near-infrared wavelength range.

Further, in FIG. 1D, two absorption layers 11a and 11b may either be the same or different. When the two absorption layers 11a and 11b are different, the absorption layer 11a may be the near-infrared absorbing layer, and the absorption layer 11b may be the ultraviolet absorbing layer, or the absorption layer 11a may be the ultraviolet absorbing layer, and the absorption layer 11b may be the near-infrared absorbing layer.

Figure 1E:
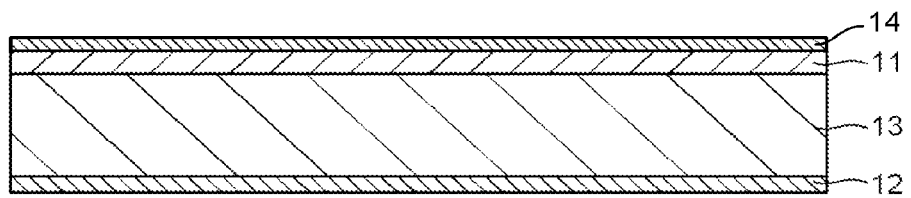
FIG. 1E is a cross-sectional view schematically illustrating another example of the NIR filter according to one embodiment.

FIG. 1E illustrates a structural example having an anti-reflection layer 14 on a main surface of the absorption layer 11 of the filter illustrated in FIG. 1B. In the case where an absorption layer is the uppermost surface as in the filter illustrated in FIG. 1B, the anti-reflection layer may be provided on the absorption layer. Note that the anti-reflection layer may be structured to cover not only the uppermost surface of the absorption layer but the entire side surfaces of the absorption layer. In this case, the moisture resistance of the absorption layer can be improved.

The present filter satisfies the following requirements (1) to (3):

(1) Average transmittance (R) in the wavelength range of 620 to 750 nm is 20% or less and average transmittance (G) in the wavelength range of 495 to 570 nm is 90% or more in a spectral transmittance curve at an incident angle of 0°, and a ratio (R)/(G) of the average transmittance is 0.2 or less.

(2) Difference $|T_{0(600-725)} - T_{30(600-725)}|$ between an integral value $T_{0(600-725)}$ of transmittance in the wavelength range of 600 to 725 nm in the spectral transmittance curve at an incident angle of 0°, and an integral value $T_{30(600-725)}$ of transmittance in the wavelength range of 600 to 725 nm in a spectral transmittance curve at an incident angle of 30° is 3%·nm or less.

(3) The filter has a wavelength $\lambda IR_{T(80)}$ at which transmittance becomes 80%, a wavelength $\lambda IR_{T(50)}$ at which transmittance becomes 50%, and a wavelength $\lambda IR_{T(20)}$ at which transmittance becomes 20% in the wavelength range of 550 to 750 nm in the spectral transmittance curve at an incident angle of 0° normalized by maximum transmittance in the wavelength range of 450 to 650 nm (hereinafter also referred to as the "normalized spectral transmittance curve at an incident angle of 0°"), and the wavelengths $\lambda IR_{T(80)}$, $\lambda IR_{T(50)}$, and $\lambda IR_{T(20)}$ satisfy following formulae (a), (b) and (c), respectively:

$$0 \leq \lambda IR_{T(20)} - \lambda_{T(80)} \leq 30 \text{ nm} \quad (a),$$

$$0 \leq \lambda IR_{T(50)} - \lambda_{T(50)} 35 \text{ nm} \quad (b),$$

$$0 \leq \lambda IR_{T(20)} - \lambda_{T(20)} \leq 37 \text{ nm} \quad (c),$$

where $\lambda_{T(80)}$, $\lambda_{T(50)}$ and $\lambda_{T(20)}$ are wavelengths on a long wavelength side where relative visibility of 0.8, 0.5 and 0.2 is exhibited in a relative visibility curve, respectively.

Satisfying the requirements (1), (3) enables to obtain a spectral curve close to the relative visibility curve, and reproduce colors from which excessive redness is removed. Satisfying the requirement (2) enables to decrease incident angle dependence of light with a wavelength of 600 to 725 nm. Consequently, differences in color reproducibility due to an incident angle can be suppressed.

As used herein, the "spectral transmittance curve at an incident angle of 0°" refers to a spectral transmittance curve of light incident perpendicularly to the main surface of an optical filter, and the "spectral transmittance curve at an incident angle of 30°" refers to a spectral transmittance curve of light incident at an angle of 30° from a direction perpendicular to the main surface of an optical filter.

In the present filter, average transmittance (R) of light in the wavelength range of 620 to 750 nm may be 20% or less, preferably 19% or less, more preferably 17% or less, even more preferably 14% or less in the spectral transmittance curve at an incident angle of 0°. The lower the average transmittance (R) of light in the wavelength range of 620 to 750 nm, the lower the transmittance of red color can be made, for which human eye's sensitivity is low.

In the present filter, average transmittance (G) of light in the wavelength range of 495 to 570 nm may be 90% or more, preferably 93% or more, more preferably 95% or more, even more preferably 97% or more in the spectral transmittance curve at an incident angle of 0°. The higher the average transmittance (G) of light in the wavelength range of 495 to 570 nm, the higher the transmittance of green color can be made, for which human eye's sensitivity is high.

In the present filter, the ratio (R)/(G) of the average transmittance is 0.20 or less, preferably 0.18 or less, more preferably 0.15 or less. The smaller the (R)/(G), the lower the transmittance of red than green, with which a spectral transmittance curve close to the relative visibility curve can be obtained.

In the present filter, $|T_{0(600-725)} - T_{30(600-725)}|$ may be 3%·nm or less, preferably 2%·nm or less, even more preferably 1%·nm or less. Note that $|T_{0(600-725)} - T_{30(600-725)}|$ is an index indicating the incident angle dependence of light of the present filter in the wavelength range of 600 to 725 nm. The smaller this value, the lower the incident angle dependence indicated by this value.

In the present filter, in the normalized spectral transmittance curve at an incident angle of 0°, the wavelengths $\lambda IR_{T(80)}$, $\lambda IR_{T(50)}$, and $\lambda IR_{T(20)}$ may be in the wavelength range of 550 to 750 nm, preferably 580 to 720 nm, even more preferably 600 to 700 nm. When the $\lambda IR_{T(80)}$, the $\lambda IR_{T(50)}$, and the $\lambda IR_{T(20)}$ are in the wavelength range of 550 to 750 nm, a spectral transmittance curve close to the relative visibility curve can be obtained.

In the present filter, the $\lambda IR_{T(80)}$, the $\lambda IR_{T(50)}$, and the $\lambda IR_{T(20)}$ satisfy the respective formulae (a), (b) and (c), and more preferably satisfy the following formulae.

$$0 \leq \lambda IR_{T(80)} - \lambda_{T(80)} \leq 25 \text{ nm}$$

$$0 \leq \lambda IR_{T(50)} - \lambda_{T(50)} \leq 32 \text{ nm}$$

$$0 \leq \lambda IR_{T(20)} - \lambda_{T(20)} \leq 35 \text{ nm}$$

As the values (however 0 or larger) of any of $\lambda IR_{T(80)} - \lambda_{T(50)}$, $\lambda IR_{T(50)} - \lambda_{T(50)}$ and $\lambda IR_{T(20)} - \lambda_{T(20)}$ become smaller, the spectral characteristic that can be provided becomes closer to the visibility of human on the long wavelength side, and the accuracy of color reproducibility on the long wavelength side can become higher.

When the $\lambda IR_{T(80)} - \lambda_{T(80)}$, $\lambda IR_{T(50)} - \lambda_{T(50)}$ and $\lambda IR_{T(20)} - \lambda_{T(20)}$ are each less than 0, that is, when the spectral transmittance of the NIR filter comes inside the relative visibility curve (short wavelength side with respect to the relative visibility curve), this results in reduction of redness, and good color reproducibility cannot be obtained. Thus, the present filter can achieve a normalized spectral transmittance curve which is close to the relative visibility curve to the degree that it is not on the short wavelength side with respect to the relative visibility curve.

The total sum of the $\lambda IR_{T(80)} - \lambda_{T(80)}$, $\lambda IR_{T(50)} - \lambda_{T(50)}$ and $\lambda IR_{T(20)} - \lambda_{T(20)}$ is 0 to 102 nm. From the viewpoint of making the spectral characteristic closer to the visibility of human, the total sum is preferably 0 to 92 nm, more preferably 0 to 80 nm. Further, when $(\lambda IR_{T(80)} - \lambda_{T(80)})/(\lambda IR_{T(50)} - \lambda_{T(50)}) \leq 1.5$, and $(\lambda IR_{T(20)} - \lambda_{T(20)})/(\lambda IR_{T(50)} - \lambda_{T(50)}) \leq 2.0$, the spectral characteristic can be made much closer to the visibility of human, which is further preferred.

Preferably, the present filter further satisfy the following requirement (9).

(9) Average transmittance in the wavelength range of 750 to 850 nm is 0.2% or less in the spectral transmittance curve at an incident angle of 0°.

When the average transmittance of this wavelength range is 0.2% or less, near-infrared light which the human eyes do not sense but the solid-state image sensing device does sense can be largely blocked, and thus an image with high contrast can be obtained. Further, the average transmittance in the wavelength range of 750 to 850 nm is preferably 0.15% or less, more preferably 0.1% or less.

The transparent substrate, the absorption layer, the reflection layer and the anti-reflection layer which constitute the present filter will be described below.

[Transparent Substrate]

The shape of the transparent substrate is not particularly limited, and may be any of a block form, a plate form, and a film form. The thickness of the transparent substrate is, although depending on the constituent material, preferably 0.03 to 5 mm, more preferably 0.05 to 1 mm from the point of thickness reduction.

The constituent material of the transparent substrate is not particularly limited as long as it transmits visible light. Examples of the material include inorganic materials such as glass and crystal, and organic materials such as resin. The inorganic materials are preferably used as the transparent substrate from the viewpoints of optical property as the optical filter, shape stability related to reliability over a long period such as a mechanical property, and handleability during manufacturing of the filter, and so on. Among them, from the viewpoint of workability, glass is preferred. Further, the organic materials are preferably used as the transparent substrate from the point of thickness reduction or the like.

Examples of resins which can be used for the transparent substrate include polyester resins such as polyethylene terephthalate and polybutylene terephthalate, polyolefin resins such as polyethylene, polypropylene, and ethylene-vinyl acetate copolymer, acrylic resins such as norbornene resin, polyacrylate, and polymethyl methacrylate, urethane resins, vinyl chloride resins, fluorocarbon resins, polycarbonate resins, polyvinyl butyral resins, polyvinyl alcohol resins, and polyimide resins.

Examples of glasses which can be used for the transparent substrate include an absorption-type glass made by adding CuO or the like to a fluorophosphate-based glass, a phosphate-based glass, or the like, a soda lime glass, a borosilicate glass, a non-alkali glass, and a quartz glass. Note that "phosphate glasses" includes a silicophosphate glass in which part of the skeleton of the glass is composed of $SiO_2$.

Further, examples of crystal materials which can be used for the transparent substrate include birefringent crystals such as crystalline quartz, lithium niobate, and sapphire. Specific composition examples of a glass containing CuO used for the transparent substrate will be described.

(1) A glass containing CuO: 0.5 to 7 part by mass in outer percentage relative to 100 part by mass of a base glass containing, in mass %, $P_2O_5$ of 46 to 70%, $AlF_3$ 0.2 to 20%, $LiF+NaF+KF$ 0 to 25%, and $MgF_2+CaF_2+SrF_2+BaF_2+PbF_2$ 1 to 50%, where F is 0.5 to 32%, 0 is 26 to 54%.

(2) A glass containing, in mass %, $P_2O_5$ of 25 to 60%, $Al_2OF_3$ 1 to 13%, MgO 1 to 10%, CaO 1 to 16%, BaO 1 to 26%, SrO 0 to 16%, ZnO 0 to 16%, $Li_2O$ 0 to 13%, $Na_2O$ 0 to 10%, $K_2O$ 0 to 11%, CuO 1 to 7%, $\Sigma RO$ (where R=Mg, Ca, Sr, Ba) 15 to 40%, and $\Sigma R'_2O$ (where R'=Li, Na, K) 3 to 18%, where $O^{2-}$ ions up to 39 mol % amount are substituted by $F^-$ ions.

(3) A glass containing, in mass %, $P_2O_5$ of 5 to 45%, $AlF_3$ 1 to 35%, RF, where R is Li, Na, K, 0 to 40%, $R'F_2$, where R' is Mg, Ca, Sr, Ba, Pb, or Zn, 10 to 75%, $R''F_m$, where R" is La, Y, Cd, Si, B, Zr, or Ta, and m is a number equivalent to the atomic value of R", 0 to 15%, where up to 70% of the total volume of fluoride may be substituted by an oxide, and CuO 0.2 to 15%.

(4) A glass containing, in cation %, $P^{5+}$ of 11 to 43%, $Al^{3+}$ 1 to 29%, R cations (total amount of Mg, Ca, Sr, Ba, Pb, and Zn ions) 14 to 50%, R' cations (total amount of Li, Na, and K ions) 0 to 43%, R" cations (total amount of La, Y, Gd, Si, B, Zr, and Ta ions) 0 to 8%, and $Cu^{2+}$ 0.5 to 13%, and further containing $F^-$ 17 to 80% in anion %.

(5) A glass containing, in cation %, $P^{5+}$ of 23 to 41%, $Al^{3+}$ 4 to 16%, $Li^+$ 11 to 40%, $Na^+$ 3 to 13%, $R^{2+}$ (total amount of $Mg^{2+}$, $Ca^{2+}$, $Sr^{2+}$, $Ba^{2+}$, and $Zn^{2+}$) 12 to 53%, and $Cu^{2+}$ 2.6 to 4.7%, and further containing, in anion %, 25 to 48% and $O^{2-}$ 52 to 75%.

(6) A glass containing CuO: 0.1 to 5 part by mass in outer percentage relative to 100 part by mass of a base glass containing, in mass %, $P_2O_5$ of 70 to 85%, $Al_2O_3$ 8 to 17%, $B_2O_3$ 1 to 10%, $Li_2O$ 0 to 3%, $Na_2O$ 0 to 5%, and $K_2O$ 0 to 5%, where $Li_2O+Na_2O+K_2O$ 0.1 to 5%, and $SiO_2$ 0 to 3%.

Examples of the commercial products of such glass include NF-50E, NF-50EX, NF-50T, NF-50TX (product name, manufactured by Asahi Glass Co., Ltd.) for the glass of (1), BG-60, BG-61 (product name, manufactured by Schott AG) for the glass of (2), and CD 5000 (product name, manufactured by HOYA Corporation) for the glass of (5).

The above-described CuO-containing glasses may further contain a metal oxide. For example, when one kind or two or more kinds of $Fe_2O_3$, $MoO_3$, $WO_3$, $CeO_2$, $Sb_2O_3$, $V_2O_5$, and the like are contained as the metal oxide, the CuO-containing glasses have an ultraviolet absorbing property. The content of these metal oxides is preferably such that at least one kind selected from the group consisting of $Fe_2O_3$, $MoO_3$, $WO_3$, and $CeO_2$ is contained by $Fe_2O_3$ of 0.6 to 5 part by mass, $MoO_3$ 0.5 to 5 part by mass, $WO_3$ 1 to 6 part by mass, and $CeO_2$ 2.5 to 6 part by mass, or two kinds of $Fe_2O_3$ and $Sb_2O_3$ are contained by $Fe_2O_3$ of 0.6 to 5 part by mass+$Sb_2O_3$ of 0.1 to 5 part by mass, or two kinds of $V_2O_5$ and $CeO_2$ are contained by $V_2O_5$ of 0.01 to 0.5 part by mass+$CeO_2$ of 1 to 6 part by mass, relative to the CuO-containing glass 100 part by mass.

The optical property of the transparent substrate just needs to satisfy the optical property of the present invention when it constitutes an NIR filter obtained by stacking an absorption layer, a reflection layer, and/or the like.

The transparent substrate may, when the absorption layer below is to be stacked on its main surface, be subjected to a surface treatment with a silane coupling agent on its stacking surface. Use of the transparent substrate which is subjected to the surface treatment can increase adhesiveness to the absorption layer. Regarding the silane coupling agent, for example, the same one as that used for the absorption layer below can be used.

[Absorption Layer]

The absorption layer is a layer containing a near-infrared absorbing material (A) and a transparent resin (B), and typically is a layer in which the near-infrared absorbing material (A) is uniformly dispersed in the transparent resin (B). Preferably, the absorption layer further contains an ultraviolet absorbing material (U).

As the absorption layer, a plurality of absorption layers may be provided including, for example, a layer containing the near-infrared absorbing material (A) and a layer containing the ultraviolet absorbing material (U) as different layers.

The thickness of the absorption layer is preferably 0.1 to 100 μm. When the absorption layer is constituted of a plurality of absorption layers, the total thickness of the absorption layers is preferably 0.1 to 100 μm. The thickness of the absorption layer is determined depending on applications. When the thickness is less than 0.1 μm, it is possible that a desired optical property cannot be exhibited sufficiently. Further, when the thickness exceeds 100 μm, flatness decreases and it is possible that in-plane ununiform dispersion of absorptance occurs. The thickness of the absorption layer is more preferably 0.3 to 50 μm. When the thickness is 0.3 to 50 μm, a further sufficient optical property and flatness of layers can both be achieved.

In the present filter, typically, a near-infrared absorbing dye is used as the near-infrared absorbing material (A) and an ultraviolet absorbing dye is used as the ultraviolet absorbing material (U), but the materials are not particularly limited to them. The near-infrared absorbing dyes and the ultraviolet absorbing dyes which are typically used will be described in detail below.

(Near-Infrared Absorbing Dye (A))

The near-infrared absorbing dye (A) (hereinafter also referred to as a dye (A)) is not limited in particular as long as it is has an ability to transmit light in the visible wavelength range (450 to 600 nm) and to absorb light in the near-infrared wavelength range (700 to 1100 nm). The dye may be a pigment, that is, may be in a state of being an aggregate of molecules. Hereinafter, the near-infrared absorbing dye may be referred to as a "NIR absorbing dye" as necessary.

The dye (A) is preferably one exhibiting the maximum absorption wavelength in the wavelength range of 650 to 900 nm, more preferably 650 to 750 nm, in the absorption spectrum of light in the wavelength range of 400 to 900 nm measured by using a resin film obtained by dispersing the dye (A) in the transparent resin (B). A near-infrared absorbing dye having such absorbing property is herein referred to as a dye (A1). The maximum absorption wavelength in the absorption spectrum is referred to as λmax of the dye (A1). Note that, the absorption spectrum of the dye (A1) has an absorption peak having an apex of absorption at a wavelength $\lambda_{max}$ (hereinafter referred to as an "absorption peak of $\lambda_{max}$"). In the absorption spectrum of the dye (A1), in addition to having the $\lambda_{max}$ in the wavelength of 650 to 900 nm, preferably, absorption of visible light is small, and the inclination on the visible light side when seen from the absorption peak of $\lambda_{max}$ is steep. Moreover, the absorption peak of the $\lambda_{max}$ preferably has a gradual inclination on the long wavelength side (the side opposite to the visible light side when seen from the absorption peak).

Examples of the dye (A1) include a cyanine-based compound, a phthalocyanine-based compound, a naphthalocyanine-based compound, a dithiol metal complex-based compound, a diimonium-based compound, a polymethine-based compound, a phthalide compound, a naphthoquinone-based compound, an anthraquinone-based compound, an indophenol-based compound, and a squarylium-based compound.

Among them, the squarylium-based compound, the cyanine-based compound, and the phthalocyanine-based compound are more preferred, and the squarylium-based compound is particularly preferred. The dye (A1) of the squarylium-based compound is preferred because its absorption of visible light is small and the absorption peak of the $\lambda_{max}$ has a steep inclination on the visible light side in the absorption spectrum, and storage stability and stability with respect to light are high. The dye (A1) of the cyanine-based compound is preferred because its absorption of visible light is small in the absorption spectrum, and absorptance of light on the long wavelength side is high in the vicinity of the $\lambda_{max}$. Further, the cyanine-based compound secures long-term stability by forming salt. The dye (A1) of the phthalocyanine-based compound is preferred because of its excellence in heat resistance and weather resistance.

One example of the dye (A1) which is the squarylium-based compound is, specifically, at least one kind selected from squarylium-based compounds of the formula (F1). a chemical compound of the formula (F1) will also be called a chemical compound (F1) herein. The same applies to any other chemical compound.

The chemical compound (F1) is a squarylium-based compound having a structure in which benzene rings are bonded to the left and right sides of a squarylium skeleton, nitrogen atoms are further bonded to fourth positions of the benzene rings, and saturated heterocycles including the nitrogen atoms are formed, and is a chemical compound having a light absorbing property as the dye (A1). In the chemical compound (F1), substituents of the benzene rings can be adjusted appropriately in the following ranges according to other required properties such as increasing solubility to a solvent used when the near-infrared absorbing layer is formed (hereinafter also referred to as a "host solvent") or to the transparent resin (B), or the like.

[Chemical 1]

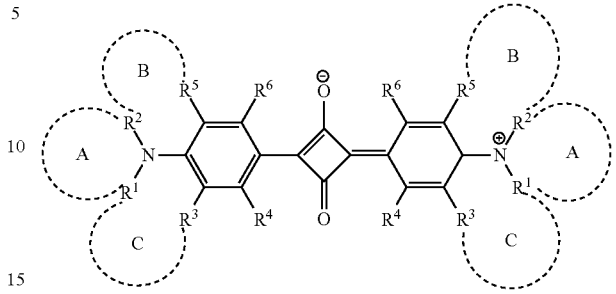

(F1)

Symbols in the formula (F1) are as follows.

Each of $R^4$ and $R^6$ independently represents a hydrogen atom, a halogen atom, a hydroxyl group, a $C_1$-$C_6$ alkyl or alkoxy group, a $C_1$-$C_{10}$ acyloxy group, or —$NR^7R^8$ where $R^7$ and $R^8$ each independently represent a hydrogen atom, a $C_1$-$C_{20}$ alkyl group, or —C(=O)—$R^9$ (where $R^9$ is a hydrogen atom, a $C_1$-$C_{20}$ alkyl group which may have a substituent or a $C_6$-$C_{11}$ aryl group, or a $C_7$-$C_{18}$ alaryl group which may have a substituent and may have an oxygen atom between carbon atoms).

At least one of $R^1$ and $R^2$, $R^2$ and $R^5$, and $R^1$ and $R^3$ may form 5- or 6-membered heterocycles A, B, and C together with a nitrogen atom.

$R^1$ and $R^2$ when the heterocycle A is formed represent, as a bivalent group -Q- in which they are bonded, an alkylene group or an alkyleneoxy group, in which hydrogen atoms may be substituted by a $C_1$-$C_6$ alkyl group, a $C_6$-$C_{10}$ aryl group, or a $C_1$-$C_{10}$ acyloxy group which may have a substituent.

$R^2$ and $R^5$ when the heterocycle B is formed and $R^1$ and $R^3$ when the heterocycle C is formed represent, each as a bivalent group —$X^1$—$Y^1$— and —$X^2$—$Y^2$— in which they are bonded (the side bonded to nitrogen is $X^1$ or $X^2$), a group in which each of $X^1$ and $X^2$ is represented by following formulae (1x) or (2x) and a group in which each of $Y^1$ and $Y^2$ is represented by one selected from following formulae (1y) to (5y). When each of $X^1$ and $X^2$ is a group of the formula (2x), $Y^1$ and $Y^2$ may each be a direct bond.

[Chemical 2]

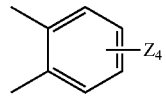

(1x)

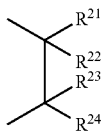

(2x)

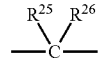

(1y)

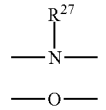

(2y)

(3y)

-continued $$—S—\quad (4y)$$
$$—Se—\quad (5y)$$

In formula (1x), four Zs each independently represent a hydrogen atom, a hydroxyl group, a $C_1$-$C_6$ alkyl or alkoxy group, or —$NR^{28}R^{29}$, where $R^{28}$ and $R^{29}$ each independently represent a hydrogen atom or a $C_1$-$C_{20}$ alkyl group. $R^{21}$ to $R^{26}$ each independently represent a hydrogen atom, a $C_1$-$C_6$ alkyl group or a $C_6$-$C_{10}$ aryl group, and $R^{27}$ represents a $C_1$-$C_6$ alkyl group or a $C_6$-$C_{10}$ aryl group.

$R^7$, $R^8$, $R^9$, $R^4$, $R^6$, $R^{21}$ to $R^{27}$, $R^1$ to $R^3$ when the heterocycles are not formed, and $R^5$ may be bonded to another one of them to form a 5- or 6-membered ring. $R^{21}$ and $R^{26}$, and $R^{21}$ and $R^{27}$ may be bonded directly.

$R^1$ and $R^2$ when the heterocycle is not formed each independently represent a hydrogen atom, a $C_1$-$C_6$ alkyl or allyl group which may have a substituent, or a $C_6$-$C_{11}$ aryl or alaryl group. $R^3$ and $R^5$ when the heterocycles are not formed each independently represent a hydrogen atom, a halogen atom, or a $C_1$-$C_6$ alkyl or alkoxy group. Hereinafter, the heterocycle A may simply be referred to as a ring A. The same applies to the heterocycle B and the heterocycle C.

In the chemical compound (F1), $R^4$ and $R^6$ each independently represent the above atoms or groups. Examples of the halogen atom include a fluorine atom, a chlorine atom, a bromine atom, or the like. The alkyl group may be linear, branched or cyclic. $R^4$ and $R^6$ are preferably of a combination in which one of them is a hydrogen atom and the other is —$NR^7R^8$.

When the chemical compound (F1) has only the ring A, only the ring B and the ring C, or the ring A to the ring C out of the ring A to the ring C, —$NR^7R^8$ may be introduced into either of $R^4$ and $R^6$. When the chemical compound (F1) has only the ring B, or only the ring A and the ring B, —$NR^7R^8$ is preferably introduced into $R^4$. Similarly, when the chemical compound has only the ring C, or only the ring A and the ring C, —$NR^7R^8$ is preferably introduced into $R^6$.

As the —$NR^7R^8$, from the viewpoint of solubility to a host solvent or to the transparent resin (B), —NH—C(=O)—$R^9$ is preferred. $R^9$ is preferably a $C_1$-$C_{20}$ alkyl group which may have a substituent, a $C_6$-$C_{10}$ aryl group which may have a substituent, or a $C_7$-$C_{18}$ alaryl group which may have a substituent and may have an oxygen atom between carbon atoms. Examples of the substituent include a halogen atom such as a fluorine atom, a hydroxyl group, a carboxy group, a sulfo group, a cyano group, a $C_1$-$C_6$ alkyl group, a $C_1$-$C_6$ fluoroalkyl group, a $C_1$-$C_6$ alkoxy group, and a $C_1$-$C_6$ acyloxy group.

Among them, $R^9$ is preferably a group selected from a $C_1$-$C_{17}$ linear, branched or cyclic alkyl group which may be substituted by a fluorine atom, a phenyl group which may be substituted by a $C_1$-$C_6$ fluoroalkyl group, and/or a $C_1$-$C_6$ alkoxy group, and a $C_7$-$C_{18}$ alaryl group which may have an oxygen atom between carbon atoms and has, on its terminal, a $C_1$-$C_6$ alkyl group which may be substituted by a fluorine atom and/or a phenyl group which may be substituted by a $C_1$-$C_6$ alkoxy group.

As $R^9$, a group can be preferably used which is a $C_5$-$C_{25}$ hydrocarbon group having at least one branch, in which one or more hydrogen atoms may be independently substituted by a halogen atom, a hydroxyl group, a carboxy group, a sulfo group, or a cyano group, and which may include an unsaturated bond, an oxygen atom, or a saturated or unsaturated ring structure between carbon atoms. Examples of such $R^9$ include groups represented by formulae (1a), (1b), (2a) to (2e), (3a) to (3e) below.

[Chemical 3]

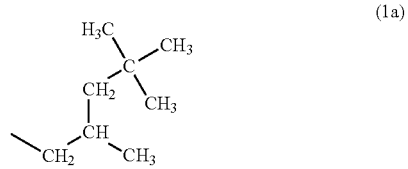
(1a)

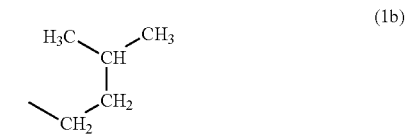
(1b)

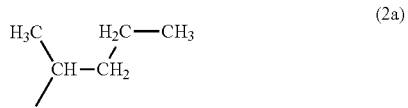
(2a)

(2b)

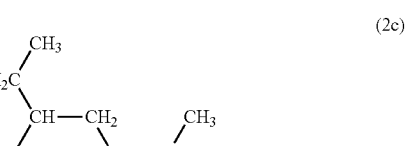
(2c)

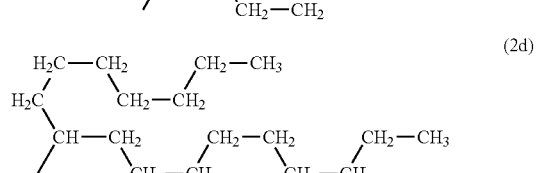
(2d)

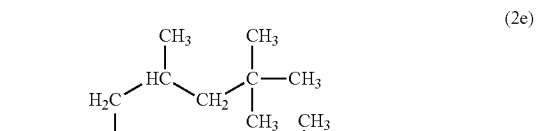
(2e)

[Chemical 4]

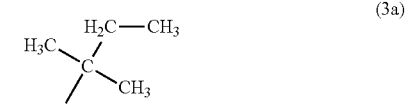
(3a)

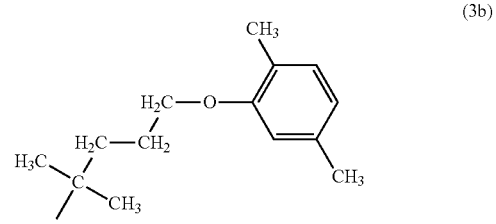
(3b)

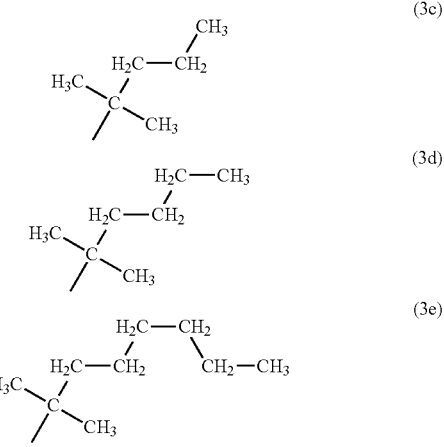

In the chemical compound (F1), regarding the ring A, the ring B, and the ring C with a ring number of 5 or 6 formed of $R^1$ and $R^2$, $R^2$ and $R^5$, and $R^1$ and $R^3$ coupled to each other, at least one of them may be formed, or two or three of them may be formed.

$R^1$ and $R^2$ when the rings are not formed each independently represent a hydrogen atom, a $C_1$-$C_6$ alkyl or allyl group which may have a substituent, or a $C_6$-$C_{11}$ aryl or alaryl group. The alkyl group may be linear, branched or cyclic. Examples of the substituent include a hydroxyl group, a $C_1$-$C_3$ alkoxy group, and a $C_1$-$C_3$ acyloxy group. $R^3$ and $R^5$ when the rings are not formed each independently represent a hydrogen atom, a halogen atom, or a $C_1$-$C_6$ alkyl or alkoxy group. Among them, as $R^1$, $R^2$, $R^3$, $R^5$, from the viewpoint of solubility to the host solvent or the transparent resin (B), a $C_1$-$C_3$ alkyl group is preferred, and a methyl group, an ethyl group, or a 2-propyl group is particularly preferred.

Further, in the chemical compound (F1), $R^1$ to $R^6$ which the benzene rings bonded to the left and right sides of a squarylium skeleton have may be different on the left and right sides, but is preferred to be the same on the left and right sides.

Note that the chemical compound (F1) contains a chemical compound (F1-1) expressed by a formula (F1-1) having a resonance structure of the structure expressed by the above general formula (F1).

[Chemical 5]

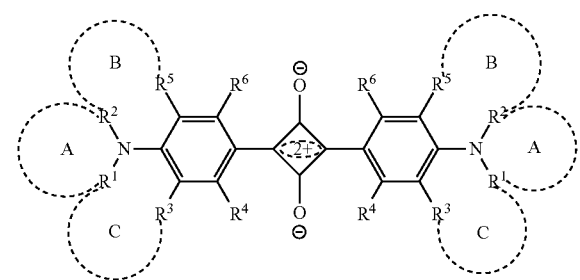

(F1-1)

The symbols in the formula (F1-1) are the same as those defined in the formula (F1).

Examples of the chemical compound (F1) more specifically include the chemical compound of a formula (F11) having only the ring B as a ring structure, the chemical compound of a formula (F12) having only the ring A as a ring structure, and the chemical compound of a formula (F13) having two of the ring B and the ring C as ring structures. Note that the chemical compound of the formula (F11) is the same chemical compound as the chemical compound having only the ring C as a ring structure in the chemical compound (F1) with $R^6$ being —$NR^7R^8$. Further, the chemical compound of the formula (F11) and the chemical compound of the formula (F13) are chemical compounds described in the U.S. Pat. No. 5,543,086.

[Chemical 6]

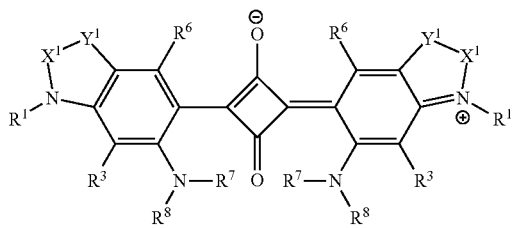

(F11)

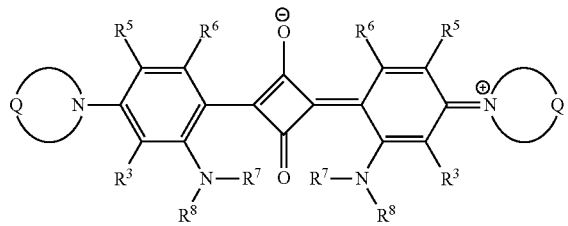

(F12)

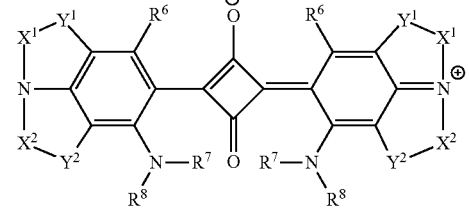

(F13)

The symbols in the formulae (F11) to (F13) are the same as those defined in the formula (F1), and the same applies to preferred modes.

In the chemical compound (F11), as $X^1$, an ethylene group in which the hydrocarbon atom may be substituted by a $C_1$-$C_6$ alkyl group or a $C_6$-$C_{10}$ aryl group expressed in the above (2x) is preferred. In this case, as the substituent, a $C_1$-$C_3$ alkyl group is preferred, and a methyl group is more preferred. Examples of $X^1$ specifically include —$(CH_2)_2$—, —$CH_2$—$C(CH_3)_2$—, —$CH(CH_3)$—$C(CH_3)_2$—, and —$C(CH_3)_2$—$C(CH_3)_2$—. As the —$NR^7R^8$ in chemical compound (F11), —NH—C(=O)—$CH_3$, —NH—C(=O)—$C_6H_{13}$, —NH—C(=O)—$C_6H_5$, —NH—C(=O)—CH($C_2H_5$)—$C_4H_9$, —NH—C(=O)—C($CH_3$)$_2$—$C_2H_5$, —NH—C(=O)—C($CH_3$)$_2$—$C_3H_7$, —NH—C(=O)—C($CH_3$)$_2$—$(CH_2)_3$—O—$C_6H_3(CH_3)_2$, or the like is preferred.

Examples of the chemical compound (F11) include chemical compounds expressed by formulae (F11-1) to formula (F11-7). Among them, due to high solubility to the host solvent and the transparent resin (B), the chemical compounds (F11-2) to (F11-7) are more preferred.

[Chemical 7]

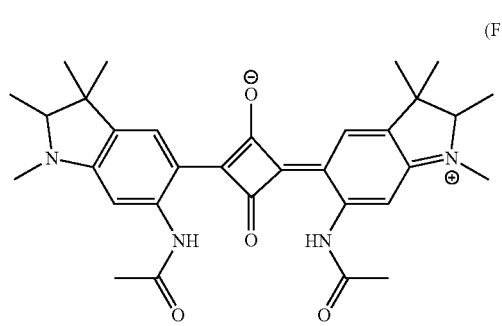
(F11-1)

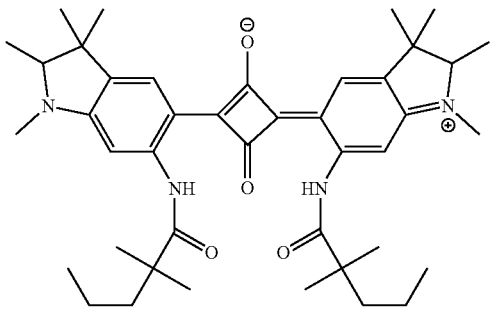
(F11-5)

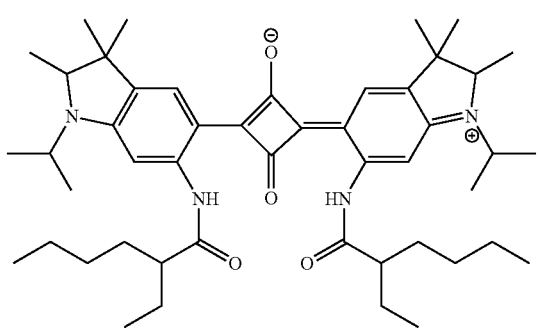
(F11-2)

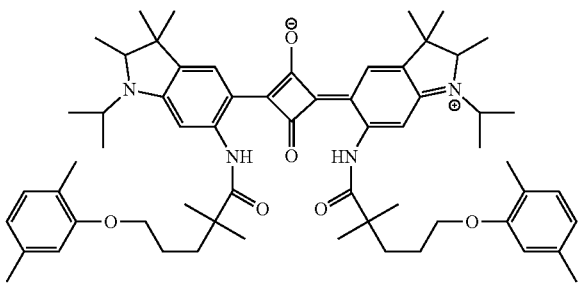
(F11-6)

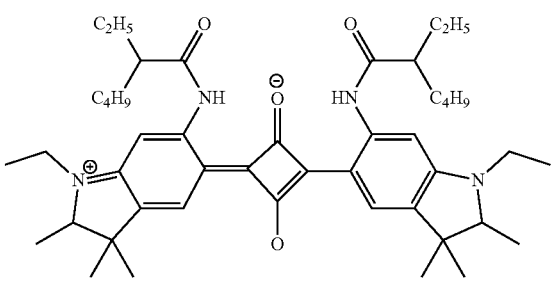
(F11-7)

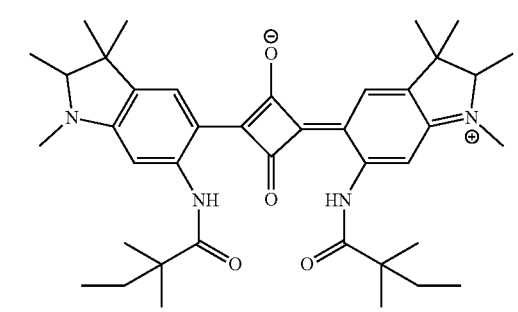
(F11-3)

[Chemical 8]

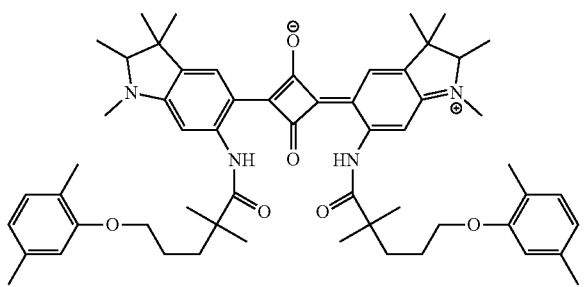
(F11-4)

In the chemical compound (F12), Q is a $C_4$ or $C_5$ alkylene group or a $C_3$ or $C_4$ alkyleneoxy group, in which hydrogen atoms may be substituted by a $C_1$-$C_6$ alkyl group, a $C_6$-$C_{10}$ aryl group, or a $C_1$-$C_{10}$ acyloxy group which may have a substituent. The position of oxygen in the case of the alkyleneoxy group is preferably other than where it is adjacent to N. As Q, a butylene group which may be substituted by a $C_1$-$C_3$ alkyl group, particularly a methyl group is preferred.

In the chemical compound (F12), as —NR$^7$R$^8$, —NH—C(=O)—(CH$_2$)$_m$—CH$_3$ (where m is 0 to 19), —NH—C(=O)-Ph-R$^{10}$ (where -Ph- represents a phenylene group, and R$^{10}$ represents a hydrogen atom, a $C_1$-$C_3$ alkyl group in which a hydrogen atom may be substituted by a fluorine atom, or a $C_1$-$C_3$ alkoxy group), or the like is preferred.

Since the $\lambda_{max}$ of the chemical compound (F12) is on the relatively long wavelength side in the above-described wavelength range, using the chemical compound (F12) can widen the transmission region of visible light. Examples of the chemical compound (F12) include chemical compounds represented by formulae (F12-1) to (F12-3).

[Chemical 9]

(F12-1)
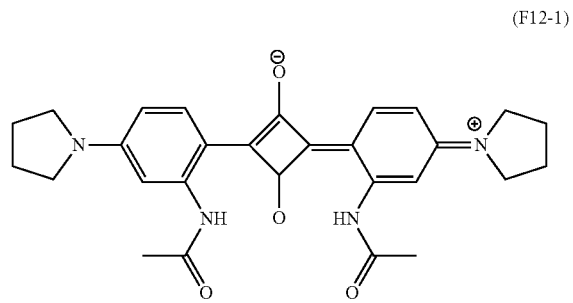

(F12-2)
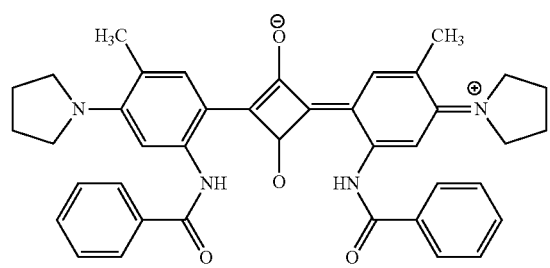

(F12-3)
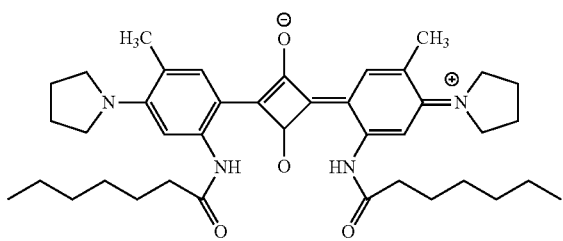

In the chemical compound (F13), preferably $X^1$ and $X^2$ are independently an ethylene group expressed by the above (2x) in which the hydrogen atom may be substituted by a $C_1$-$C_6$ alkyl group or a $C_6$-$C_{10}$ aryl group. In this case, the substituent is preferably a $C_1$-$C_3$ alkyl group, more preferably a methyl group. $X^1$ and $X^2$ may be, specifically, —($CH_2$)$_2$—, —$CH_2$—C($CH_3$)$_2$—, —CH($CH_3$)—C($CH_3$)$_2$—, —C($CH_3$)$_2$—C($CH_3$)$_2$—, and the like. $Y^1$ and $Y^2$ may be, independently, —$CH_2$—, —C($CH_3$)$_2$—, —CH($C_6H_5$)—, —CH(($CH_2$)$_m$$CH_3$)— (where m is 0 to 5), and the like. In the chemical compound (F13), —$NR^7R^8$ is preferably —NH—C(=O)—$C_mH_{2m+1}$ (where m is 1 to 20, and $C_mH_{2m+1}$ may be linear, branched, or cyclic), —NH—C(=O)-Ph-$R^{10}$ (where -Ph- represents a phenylene group, and $R^{10}$ represents a hydrogen atom, a $C_1$-$C_3$ alkyl group, a $C_1$-$C_3$ alkoxy group, or a $C_1$-$C_3$ perfluoroalkyl group), or the like.

Examples of the chemical compound (F13) include chemical compounds of a formula (F13-1) and a formula (F13-2).

[Chemical 10]

(F13-1)
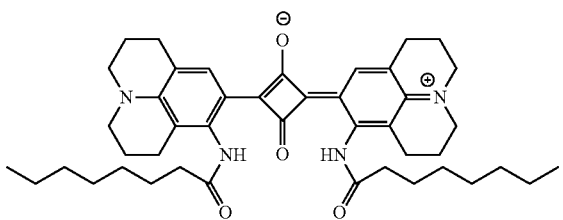

(F13-2)
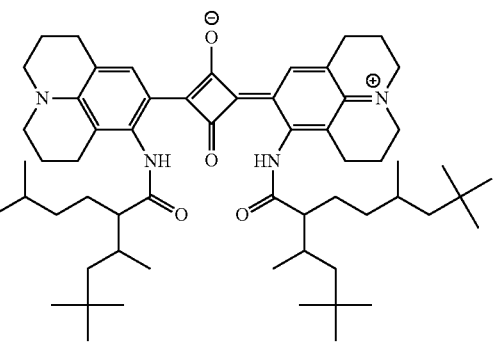

Further, as a dye (A1), a squarylium-based compound of the formula (F6) can also be used. The formula (F6) expresses a chemical compound in which none of the ring A to the ring C is formed in the formula (F1), where $R^1$ to $R^6$ are as follows.

[Chemical 11]

(F6)
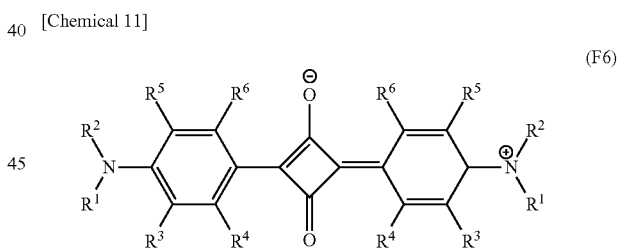

Symbols in the formula (F6) are as follows.

$R^1$ and $R^2$ each independently represent a hydrogen atom, a $C_1$-$C_{12}$ alkyl or allyl group which may have a substituent, or a $C_6$-$C_{11}$ aryl or alaryl group. $R^3$ and $R^5$ each independently represent a hydrogen atom, a halogen atom, or a $C_1$-$C_6$ alkyl or alkoxy group. $R^4$ and $R^6$ each independently represent a hydrogen atom, a halogen atom, a hydroxyl group, or a $C_1$-$C_6$ alkyl or alkoxy group, a $C_1$-$C_{10}$ acyloxy group, or —$NR^7R^8$, where $R^7$ and $R^8$ each independently represent a hydrogen atom, a $C_1$-$C_{20}$ alkyl group, or —C(=O)—$R^9$, where $R^9$ is a hydrogen atom, a $C_1$-$C_{20}$ alkyl group or a $C_6$-$C_{11}$ aryl group which may have a substituent, or a $C_7$-$C_{18}$ alaryl group which may have a substituent and may have an oxygen atom between carbon atoms.

Examples of the chemical compound (F6) include chemical compounds of a formula (F6-1) and a formula (F6-2).

[Chemical 12]

(F6-1)

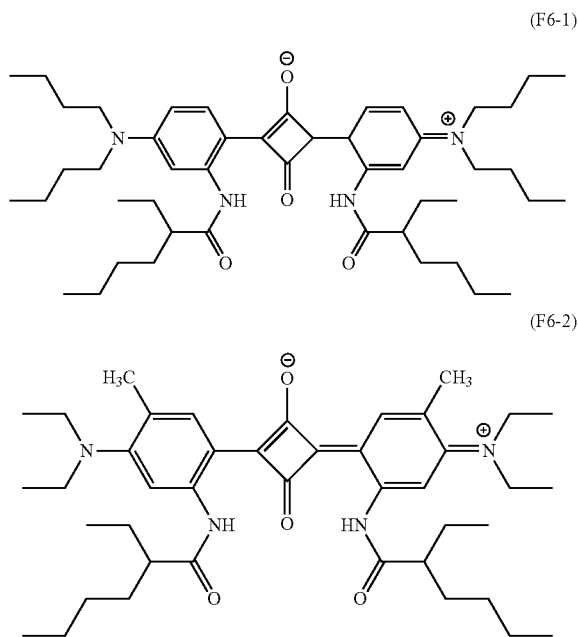

(F6-2)

Moreover, as the dye (A1), a squarylium-based chemical compound of a formula (F7) can also be used.

[Chemical 13]

(F7)

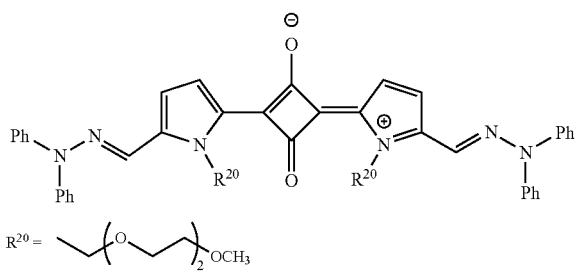

The chemical compound (F1) such as the chemical compound (F11), the chemical compound (F12), or the chemical compound (F13), as well as the chemical compound (F6) and the chemical compound (F7) can be produced by a conventionally known method. The chemical compound (F11) such as the chemical compound (F11-1) can be produced by a method described in, for example, U.S. Pat. No. 5,543,086. Further, the chemical compound (F12) can be produced by a method described in, for example, J. Org. Chem. 2005, 70 (13), 5164-5173.

As the dye (A1) which is a squarylium-based compound, a commercial product may be used. Examples of the commercial product include 52098 and 52084 (product names, manufactured by FEW Chemicals).

The dye (A1) which is a cyanine-based compound may be, specifically, at least one selected from cyanine-based compounds expressed by a formula (F5).

[Chemical 14]

(F5)

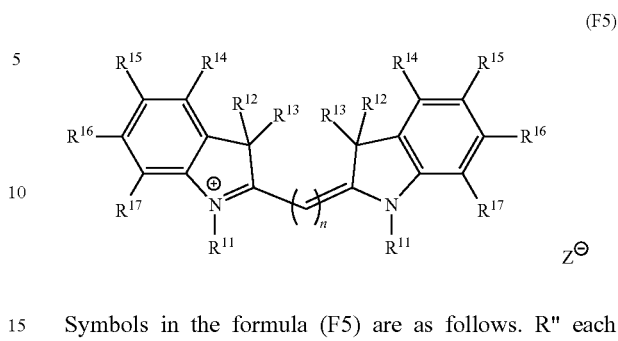

Symbols in the formula (F5) are as follows. R" each independently represents a $C_1$-$C_{20}$ alkyl group, alkoxy group or alkyl sulfone group, or an anion species thereof. $R^{12}$ and $R^{13}$ each independently represent a hydrogen atom or a $C_1$-$C_{20}$ alkyl group.

Z represents a $PF_6$, $ClO_4$, $R^f$—$SO_2$, $(R^f$—$SO_2)_2$—N where $R^f$ represents a $C_1$-$C_8$ alkyl group in which at least one hydrogen atom is substituted by a fluorine atom, or $BF_4$. $R^{14}$, $R^{15}$, $R^{16}$ and $R^{17}$ each independently represent a hydrogen atom, a halogen atom, or a $C_1$-$C_6$ alkyl group. n represents an integer of 1 to 6.

$R^{11}$ in the chemical compound (F5) is preferably a $C_1$-$C_{20}$ alkyl group, and $R^{12}$ and $R^{13}$ are each independently preferably a hydrogen atom or a $C_1$-$C_6$ alkyl group. $R^{14}$, $R^{15}$, $R^{16}$ and $R^{17}$ are each independently preferably a hydrogen atom, and n is preferably 1 to 4. The structure of the left and right sides across n repetitive units may be different, but is preferably the same structure.

As the chemical compound (F5), a chemical compound of a formula (F51), and a chemical compound of a formula (F52), are exemplified. The anion represented by $Z^-$ is similar to $Z^-$ in the chemical compound (F5).

[Chemical 15]

(F51)

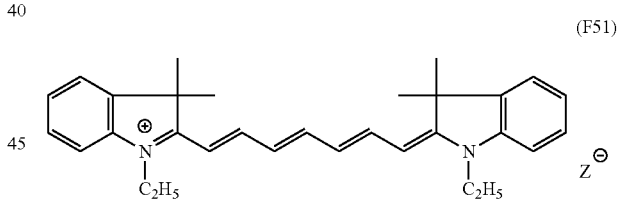

[Chemical 16]

(F52)

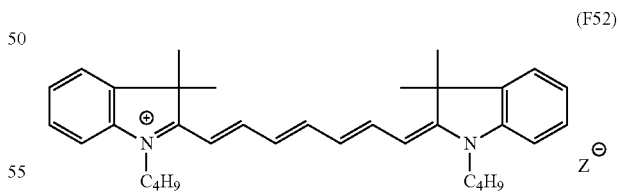

As the dye (A1) which is a cyanine-based compound, a commercial product may be used. Examples of the commercial product include ADS680HO (product name, manufactured by American Dye), S0830 (product name, manufactured by FEW Chemicals), and S2173 (product name, manufactured by FEW Chemicals).

Further, examples of a phthalocyanine-based chemical compound usable as the dye (A1) include commercial products such as FB22 (product name, manufactured by Yamada Chemical Co., Ltd.), TXEX720 (product name, manufactured by Nippon Shokubai Co., Ltd.), and PC142c (product name, manufactured by Yamada Chemical Co., Ltd.).

The $\lambda_{max}$ of chemical compounds used as the dye (A1) exemplified above are presented in Table 1 together with the types of the transparent resins (B) used at the time of measurement.

TABLE 1

| Dye type | Abbr. chemical compound or product name | Structure formula | Transparent resin (B) product name | λmax [nm] |
|---|---|---|---|---|
| Squarylium-based chemical compound | F11-1 | F11-1 | B-OKP2 | 711 |
| | F11-2 | F11-2 | B-OKP2 | 715 |
| | F11-3 | F11-3 | B-OKP2 | 706 |
| | F11-4 | F11-4 | B-OKP2 | 705 |
| | F11-4 | F11-4 | SP3810 | 704 |
| | F11-5 | F11-5 | OKP850 | 706 |
| | F11-7 | F11-7 | OKP850 | 714 |
| | F12-1 | F12-1 | B-OKP2 | 686 |
| | F12-2 | F12-2 | B-OKP2 | 715 |
| | F12-3 | F12-3 | B-OKP2 | 711 |
| | F13-1 | F13-1 | B-OKP2 | 715 |
| | F13-2 | F13-2 | B-OKP2 | 715 |
| | F7 | F7 | B-OKP2 | 734 |
| | S2084 | — | EA-F5003 | 679 |
| Cyanine-based compound | F51 | F51 | B-OKP2 | 740 |
| | F52 | F52 | B-OKP2 | 747 |
| | ADS680HO | — | EA-F5003 | 694 |
| Phthalocyanine-based compound | FB22 | — | Vylon103 | 681 |

Note that the B-OKP2 and Vylon (registered trademark) 103 used above as the transparent resin (B) are polyester resins, SP3810 is a polycarbonate resin, and EA-F5003 is an acrylic resin, details of which are as will be described later.

In this embodiment, one kind selected from a plurality of chemical compounds having a light absorbing property of the dye (A1) may be used solely, or two kinds or more selected therefrom may be used together.
The dye (A) preferably contains one kind or two or more kinds of the dye (A1). Note that the dye (A) may contain any NIR absorbing dye as necessary other than the dye (A1). When a plurality of NIR absorbing dyes are used as the dye (A), it is preferred to use the NIR absorbing dyes in combination so that the maximum absorption wavelength appears in the wavelength of 650 to 900 nm, or more preferred to use them so that the maximum absorption wavelength appears in the wavelength of 650 to 750 nm, in an absorption spectrum of light in the wavelength range of 400 to 900 nm measured with respect to a resin film produced by dispersing the dyes in the transparent resin (B). Moreover, it is preferred to use the NIR absorbing dyes in combination so that absorption of visible light is small, an inclination on the visible light side is steep when seen from the absorption peak of $\lambda_{max}$, and the inclination is gradual on the long wavelength side (the side opposite to the visible light side when seen from the absorption peak) in this absorption spectrum.

The content of the dye (A) in the absorption layer is preferably 0.1 to 30 mass %, more preferably 0.5 to 25 mass %, even more preferably 1 to 20 mass % relative to the mass of the transparent resin (B). Having 0.1 mass % or more allows obtaining a desired near-infrared absorbing capability, and having 30 mass % or less suppresses decrease in near-infrared absorbing capability and increase in haze value, and the like. As the dye (A), one kind may be used solely, or two or more kinds may be mixed and used.

(Ultraviolet Absorbing Dye (U))

The ultraviolet absorbing dye (U) (hereinafter also be referred to as a dye (U)) is a chemical compound absorbing light with a wavelength of 430 nm or less. As the dye (U), a chemical compound satisfying requirements (iv-1) and (iv-2) below is preferred.

(iv-1) The absorber has at least one maximum absorption wavelength at a wavelength of 415 nm or less in a light absorption spectrum of a wavelength of 350 to 800 nm measured after dissolved in dichloromethane, and the maximum absorption wavelength $\lambda_{max}(UV)$ on the longest wavelength side in the maximum absorption in a wavelength of 415 nm or less is in the wavelength range of 360 to 415 nm.

(iv-2) When transmittance in the maximum absorption wavelength $\lambda_{max}(UV)$ is 10% in a spectral transmittance curve measured after dissolved in dichloromethane, a difference $\lambda_{L90}-\lambda_{L50}$ between a wavelength $\lambda_{L90}$ at which transmittance becomes 90% at a longer wavelength than the maximum absorption wavelength $\lambda_{max}(UV)$ and a wavelength $\lambda_{L50}$ at which transmittance becomes 50% at a longer wavelength than the maximum absorption wavelength $\lambda_{max}(UV)$ is 13 nm or less.

The maximum absorption wavelength of the dye (U) satisfying the requirement (iv-1) does not change largely in the transparent resin. That is, the dye (U) satisfying (iv-1) is preferred because the maximum absorption wavelength $\lambda_{max \cdot P}(UV)$ in an in-resin absorption spectrum exists approximately within the wavelength range of 360 to 415 nm when this dye (U) is dissolved or dispersed in the transparent resin.

The dye (U) satisfying the requirement (iv-2) exhibits excellent steepness when contained in the transparent resin. That is, also when the dye (U) is dissolved or dispersed in the transparent resin, the dye (U) satisfying (iv-2) is preferred because the difference ($\lambda_{P90}-\lambda_{P50}$) between the wavelength $\lambda_{P50}$ at which transmittance becomes 50% at a longer wavelength than the maximum absorption wavelength $\lambda_{max}(UV)$ and the wavelength $\lambda_{P90}$ at which the transmittance becomes 90% is approximately 14 nm or less, thereby exhibiting steepness equal to that in dichloromethane. Note that $\lambda_{P90}-\lambda_{P50}$ when the dye (U) is dissolved or dispersed in the transparent resin is preferably 13 nm or less, more preferably 12 nm or less.

When the dye (U) satisfying the requirement (iv-1) is used, a wavelength $\lambda_0(UV)$ and a wavelength $\lambda_{30}(UV)$ of the NIR filter in the embodiment obtained as the near-infrared absorbing layer by dissolving or dispersing it into the transparent resin can both be made to exist in a shorter wavelength range than the wavelength of 450 nm, preferably, at a wavelength of 400 to 425 nm.
When the dye (U) satisfying the requirement (iv-2) is used, in the NIR filter in the embodiment obtained as the near-infrared absorbing layer by dissolving or dispersing it into the transparent resin, the difference between the wavelength at which transmittance becomes 50% on the long wavelength side of the maximum absorption wavelength by the dye (U) and the wavelength at which the transmittance becomes 90% can be made small. That is, in this wavelength range, a change in the spectral transmittance curve can be made steep.

When the dye (U1) satisfying (iv-1) and (iv-2) is used, it is easy to make the wavelength $\lambda_0(UV)$ and the wavelength $\lambda_{30}(UV)$ exist in a region shorter than the wavelength 450 nm in the NIR filter of the embodiment, preferably a wavelength of 400 to 425 nm, and a steep change of the spectral transmittance curve in a shorter region than the wavelength 450 nm can be obtained easily.

As used herein, the absorption spectrum of light in the wavelength range of 350 to 800 nm measured when the dye (U) is dissolved in dichloromethane will also be referred to as an "absorption spectrum of the dye (U)".

The maximum absorption wavelength $\lambda_{max}(UV)$ in the absorption spectrum of the dye (U) will be referred to as the "$\lambda_{max}(UV)$ of the dye (U)".

The spectral transmittance curve measured when the dye (U) is dissolved in dichloromethane will be referred to as a "spectral transmittance curve of the dye (U)". In the spectral transmittance curve of the dye (U), when contained by an amount that makes transmittance at $\lambda_{max}(UV)$ of the dye (U) be 10%, the wavelength at which the transmittance becomes 90% at a longer wavelength than the $\lambda_{max}(UV)$ of the dye (U) will be referred to as "490", and the wavelength at which the transmittance becomes 50% at a longer wavelength than the $\lambda_{max}(UV)$ of the dye (U) will be referred to as "$\lambda_{L50}$".

Further, as used herein, the absorption spectrum of light in the wavelength range of 350 to 800 nm measured in an absorption layer produced by dissolving the dye (U) in the transparent resin (B) will also be referred to as an "in-resin absorption spectrum of the dye (U)".

The maximum absorption wavelength $\lambda_{max \cdot P}(UV)$ in the in-resin absorption spectrum of the dye (U) will be referred to as the "$\lambda_{max \cdot P}(UV)$ of the dye (U)".

A spectral transmittance curve measured in an absorption layer produced by dissolving the dye (U) in the transparent resin will be referred to as an "in-resin spectral transmittance curve of the dye (U)".

In the in-resin spectral transmittance curve of the dye (U), when contained by an amount that makes transmittance at $\lambda_{max \cdot P}(UV)$ of the dye (U) be 10%, the wavelength at which the transmittance becomes 90% at a longer wavelength than the $\lambda_{max \cdot P}(UV)$ of the dye (U) will be referred to as "$\lambda_{P90}$", and the wavelength at which the transmittance becomes 50% at a longer wavelength than the $\lambda_{max \cdot P}(UV)$ of the dye (U) will be referred to as "$\lambda_{P50}$".

The wavelength $\lambda_{max}(UV)$ of the dye (U) is preferably at a wavelength of 365 to 415 nm, more preferably at a wavelength of 370 to 410 nm. The wavelength $\lambda_{max}(UV)$ of the dye (U) being in this wavelength range makes it easy to obtain the above-described effect, namely, the steep change of the spectral transmittance curve at a wavelength of 400 to 425 nm.

Further, the difference ($\lambda_{L90}-\lambda_{L50}$) between $\lambda_{L90}$ and $\lambda_{L50}$ of the dye (U) is preferably 12 nm or less, more preferably 11 nm or less, even more preferably 9 nm or less. The $\lambda_{L90}-\lambda_{L50}$ being in this wavelength range makes it easy to obtain the above-described effect.

Examples of the dye (U1) which satisfies the requirements (iv-1) and (iv-2) include dyes of oxazole-based, merocyanine-based, cyanine-based, naphthalimide-based, oxadiazole-based, oxazine-based, oxazolidine-based, naphthalic acid-based, styryl-based, anthracene-based, cyclic carbonyl-based, and triazole-based.

Examples of oxazoles in commercial products include, Uvitex (registered trademark) OB (product name, manufactured by Ciba), Hakkol (registered trademark) RF-K (product name, manufactured by Showa Chemical Industry Co., Ltd.), Nikkafluor EFS, and Nikkafluor SB-conc (product names, manufactured by Nippon Chemical Industrial CO, LTD) Examples of merocyanines include 50511 (product name, manufactured by FEW Chemicals). Examples of cyanines include SMP370, and SMP416 (product names, manufactured by Hayashibara Co., Ltd.). Examples of naphthalimides include Lumogen (registered trademark) F violet 570 (product name, manufactured by BASF).

Examples of the dye (U1) include dyes of the general formula (N). Herein, unless otherwise particularly mentioned, the dye expressed by a formula (N) will be described as a dye (N), a dye expressed by another formula is also described similarly. Further, a group expressed by a formula (1n) will be described as a group (1n), and groups expressed by other formulae will be described similarly.

[Chemical 17]

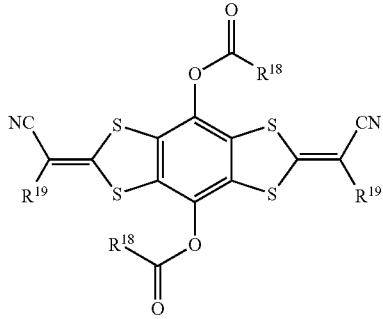

(N)

$R^{18}$ in the formula (N) may each independently represent a $C_1$-$C_{20}$ hydrocarbon group which may contain a saturated or unsaturated ring structure, and may have a branch. Specific examples of such group include an alkyl group, an alkenyl group, a saturated cyclic hydrocarbon group, an aryl group, and an alaryl group which are linear or branched. Further, in the formula (N), $R^{19}$ are each independently a cyano group or a group of the formula (n).

—COOR$^{30}$ (n)

In the formula (n), $R^{30}$ represents a $C_1$-$C_{20}$ hydrocarbon group which may contain a saturated or unsaturated ring structure, and may have a branch. Examples of such group include an alkyl group, an alkenyl group, a saturated cyclic hydrocarbon group, an aryl group, and an alaryl group which are linear or branched.

$R^{18}$ in the dye (N) are preferably, among others, a group expressed by formulae (1n) to (4n). Further, $R^{19}$ in the dye (N) are preferably, among others, a group of the formula (5n).

[Chemical 18]

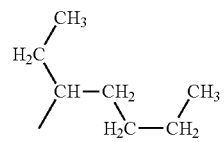

(1n)

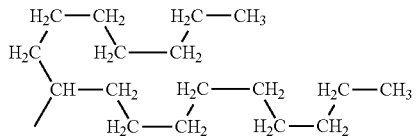

(2n)

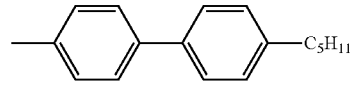

(3n)

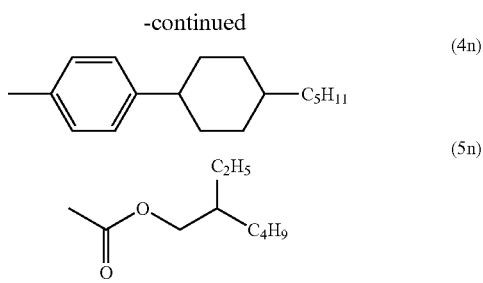

(4n)

(5n)

As specific examples of the dye (N), dyes (N-1) to (N-4) of structures presented in Table 2 can be exemplified. Note that specific structures of $R^{18}$ and $R^{19}$ in Table 2 correspond to formulae (1n) to (5n). Dye symbols are also presented in Table 2. Note that in the dyes (N-1) to (N-4), two $R^{18}$ present are the same, and $R^1$ are the same as well.

TABLE 2

| Dye symbol | $R^{18}$ | $R^{19}$ |
|---|---|---|
| N-1 | 1n | 5n |
| N-2 | 2n | 5n |
| N-3 | 3n | 5n |
| N-4 | 4n | 5n |

Among the dyes (U1) exemplified above, the dyes of oxazole-based and merocyanine-based are preferred, and examples of commercial products thereof include Uvitex (registered trademark) OB, Hakkol (registered trademark) RF-K, and S0511.

(Merocyanine-Based Dyes)
As the dye (U1), merocyanine-based dyes of the general formula (M) are particularly preferred.

[Chemical 19]

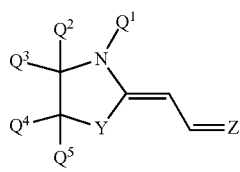

(M)

In the formula (M), Y represents an oxygen atom or a methylene group substituted by $Q^6$ and $Q^7$. Here, $Q^6$ and $Q^7$ each independently represent a hydrogen atom, a halogen atom, or a $C_1$-$C_{10}$ alkyl or alkoxy group. $Q^6$ and $Q^7$ are preferably each independently a hydrogen atom or a $C_1$-$C_{10}$ alkyl or alkoxy group, and more preferably both of them are a hydrogen atom, or one of them is a hydrogen atom and the other is a $C_1$-$C_4$ alkyl group. Particularly preferably, $Q^6$ and $Q^7$ are both a hydrogen atom.

$Q^1$ represents a monovalent hydrocarbon group with 1 to 12 carbon atoms which may have a substituent. The monovalent hydrocarbon group having no substituent is preferably a $C_1$-$C_{12}$ alkyl group in which part of hydrogen atoms may be substituted by an aliphatic ring, an aromatic ring or an alkenyl group, a $C_3$-$C_8$ cycloalkyl group in which part of hydrogen atoms may be substituted by an aromatic ring, an alkyl group or an alkenyl group, and a $C_6$-$C_{12}$ aryl group in which part of hydrogen atoms may be substituted by an aliphatic ring, an alkyl group or an alkenyl group.

When $Q^1$ is an unsubstituted alkyl group, the alkyl group may be linear or branched, and a carbon number thereof is more preferably 1 to 6.

As the $C_1$-$C_{12}$ alkyl group in which part of hydrogen atoms are substituted by an aliphatic ring, an aromatic ring or an alkenyl group, a $C_1$-$C_4$ alkyl group having a $C_3$-$C_6$ cycloalkyl group or a $C_1$-$C_4$ alkyl group substituted by a phenyl group is more preferred, and a $C_1$ or $C_2$ alkyl group substituted by a phenyl group is particularly preferred. Note that the alkyl group substituted by an alkenyl group means one which is an alkenyl group in its entirety but has no unsaturated bond between a first position and a second position, for example, an allyl group or 3-butenyl group, or the like. As the hydrocarbon group having a substituent, a hydrocarbon group having one or more of an alkoxy group, an acyl group, an acyloxy group, a cyano group, a dialkylamino group or a chlorine atom is preferred. The carbon number of these alkoxy group, acyl group, acyloxy group and dialkylamino group is preferably 1 to 6.

Preferred $Q^1$ is a $C_1$-$C_6$ alkyl group in which part of hydrogen atoms may be substituted by a cycloalkyl group or a phenyl group. Particularly preferred $Q^1$ is a $C_1$-$C_6$ alkyl group, and specific examples of such group include a methyl group, an ethyl group, a propyl group, an isopropyl group, a butyl group, an isobutyl group, and a t-butyl group.

$Q^2$ to $Q^5$ each independently represent a hydrogen atom, a halogen atom, or an alkyl group or a $C_1$-$C_{10}$ alkoxy group. The carbon number of the alkyl group and the alkoxy group is preferably 1 to 6, more preferably 1 to 4.

At least one of $Q^2$ and $Q^3$ is preferably an alkyl group, and both of them are more preferably an alkyl group. When $Q^2$ or $Q^3$ are not an alkyl group, a hydrogen atom is more preferred. Both $Q^2$ and $Q^3$ are particularly preferably a $C_1$-$C_6$ alkyl group. At least one of $Q^4$ and $Q^5$ is preferably a hydrogen atom, and more preferably both of them are a hydrogen atom. When $Q^4$ or $Q^5$ are not a hydrogen atom, a $C_1$-$C_6$ alkyl group is preferred.

Z represents any of bivalent groups expressed by formulae (Z1) to (Z5).

[Chemical 20]

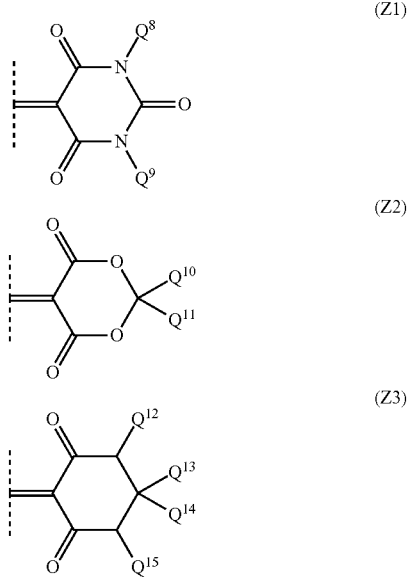

(Z1)

(Z2)

(Z3)

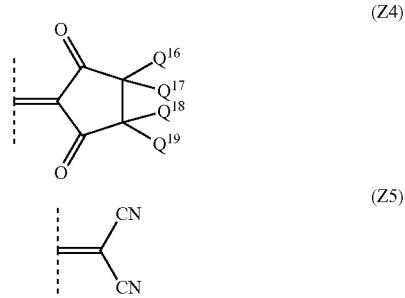

In formulae (Z1) to (Z5), $Q^8$ and $Q^9$ each independently represent a monovalent hydrocarbon group with 1 to 12 carbon atoms which may have a substituent. $Q^8$ and $Q^9$ may be different groups but preferably are the same groups.

As the monovalent hydrocarbon group which has no substituent, a $C_1$-$C_{12}$ alkyl group in which part of hydrogen atoms may be substituted by an aliphatic ring, an aromatic ring or an alkenyl group, a $C_3$-$C_8$ cycloalkyl group in which part of hydrogen atoms may be substituted by an aromatic ring, an alkyl group or an alkenyl group, or a $C_6$-$C_{12}$ aryl group in which part of hydrogen atoms may be substituted by an aliphatic ring, an alkyl group or an alkenyl group is preferred.

When $Q^8$ and $Q^9$ are an unsubstituted alkyl group, the alkyl group may be either linear or branched, and a carbon number thereof is more preferably 1 to 6. As the $C_1$-$C_{12}$ alkyl group in which part of hydrogen atoms are substituted by an aliphatic ring, an aromatic ring or an alkenyl group, a $C_1$-$C_4$ alkyl group having a $C_3$-$C_6$ cycloalkyl group and a $C_1$-$C_4$ alkyl group which is substituted by a phenyl group are more preferred, and a $C_1$ or $C_2$ alkyl group which is substituted by a phenyl group is particularly preferred. Note that the alkyl group substituted by an alkenyl group means one which is an alkenyl group in its entirety but has no unsaturated bond between a first position and a second position, such as an allyl group or 3-butenyl group As the monovalent hydrocarbon group having a substituent, a hydrocarbon group having one or more of an alkoxy group, an acyl group, an acyloxy group, a cyano group, a dialkylamino group or a chlorine atom is preferred. The carbon number of these alkoxy group, acyl group, acyloxy group and dialkylamino group is preferably 1 to 6.

$Q^8$ and $Q^9$ are preferably a $C_1$-$C_6$ alkyl group in which part of hydrogen atoms may be substituted by a cycloalkyl group or a phenyl group. Particularly preferred both $Q^8$ and $Q^9$ are a $C_1$-$C_6$ alkyl group, and specific examples of such group include a methyl group, an ethyl group, a propyl group, an isopropyl group, a butyl group, an isobutyl group or a t-butyl group.

$Q^{10}$ to $Q^{19}$ each independently represent a hydrogen atom or a monovalent hydrocarbon group with 1 to 12 carbon atoms which may have a substituent. The monovalent hydrocarbon group with 1 to 12 carbon atoms which may have a substituent is a hydrocarbon group similar to the above-described $Q^8$ and $Q^9$. As the monovalent hydrocarbon group with 1 to 12 carbon atoms which may have a substituent, an unsubstituted $C_1$-$C_6$ alkyl group is preferred.

$Q^{10}$ and $Q^{11}$ are both more preferably a $C_1$-$C_6$ alkyl group, and particularly preferably are the same alkyl group. $Q^{12}$ and $Q^{15}$ are preferably a hydrogen atom or an unsubstituted $C_1$-$C_6$ alkyl group. Any two groups bonded to the same carbon atom ($Q^{13}$ and $Q^{14}$, $Q^{16}$ and $Q^{17}$, $Q^{18}$ and $Q^{19}$) are preferably a hydrogen atom, or a $C_1$-$C_6$ alkyl group.

As the chemical compound of the formula (M), a chemical compound in which Y is an oxygen atom and Z is a group (Z1) or group (Z2), or a chemical compound in which Y is a methylene group substituted by $Q^6$ and $Q^7$ and Z is a group (Z1) or group (Z5) are preferred. As Z when Y is an oxygen atom, the group (Z1) or group (Z2) is more preferred in which $Q^1$ is a $C_1$-$C_6$ alkyl group, $Q^2$ and $Q^3$ are a hydrogen atom or a $C_1$-$C_6$ alkyl group, and $Q^4$ and $Q^5$ are both a hydrogen atom. The group (Z1) or group (Z2) in which $Q^1$ is a $C_1$-$C_6$ alkyl group, $Q^2$ and $Q^3$ are both a $C_1$-$C_6$ alkyl group, and $Q^4$ and $Q^5$ are both a hydrogen atom is particularly preferred.

In the chemical compound in which Y is a methylene group substituted by $Q^6$ and $Q^7$ and Z is the group (Z1) or group (Z5), the group (Z1) or group (Z5) is preferred in which $Q^1$ is a $C_1$-$C_6$ alkyl group, $Q^2$ and $Q^3$ are both a hydrogen atom or a $C_1$-$C_6$ alkyl group, and $Q^4$ to $Q^7$ are all a hydrogen atom, and the group (Z1) or group (Z5) in which $Q^1$ is a $C_1$-$C_6$ alkyl group and $Q^2$ to $Q^7$ are all a hydrogen atom is more preferred. As the chemical compound of the formula (M), a chemical compound in which Y is an oxygen atom and Z is the group (Z1) or group (Z2) is preferred, and a chemical compound in which Y is an oxygen atom and Z is the group (Z1) is particularly preferred.

Examples of the dye (M) include chemical compounds expressed by formulae (M-1) to (M-11).

[Chemical 21]

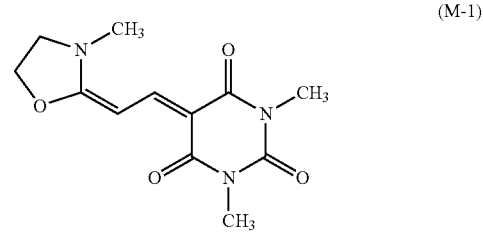

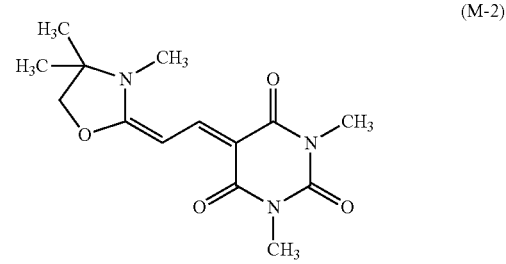

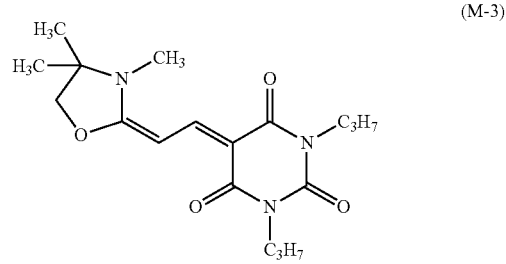

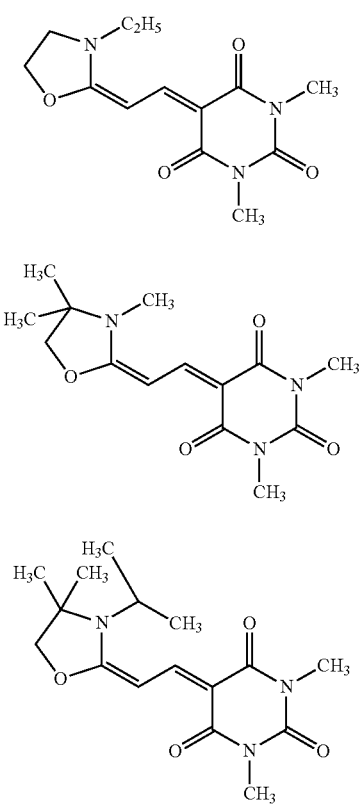

(M-4)

(M-5)

(M-6)

(M-7)

[Chemical 22]

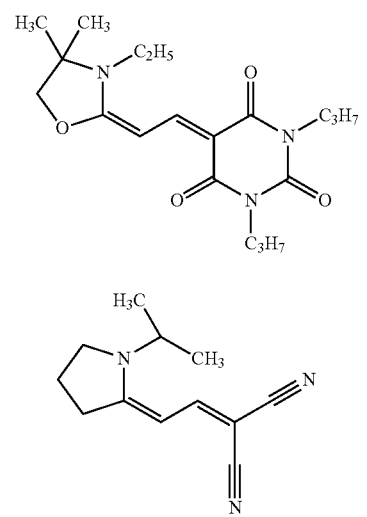

(M-8)

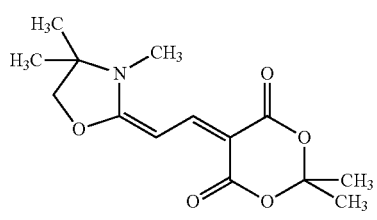

(M-9)

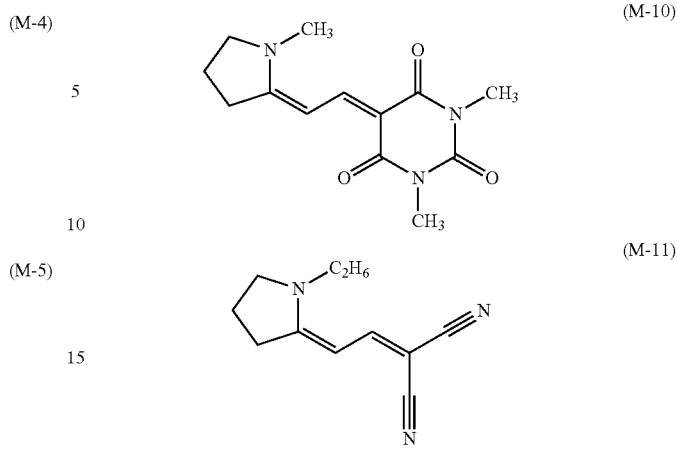

(M-10)

(M-11)

Further, as the dye (U1), ABS 407 from Exiton, UV381A, UV381B, UV382A, UV386A, VIS404A manufactured by QCR Solutions Corp., ADA1225, ADA3209, ADA3216, ADA3217, ADA3218, ADA3230, ADA5205, ADA2055, ADA6798, ADA3102, ADA3204, ADA3210, ADA2041, ADA3201, ADA3202, ADA3215, ADA3219, ADA3225, ADA3232, ADA4160, ADA5278, ADA5762, ADA6826, ADA7226, ADA4634, ADA3213, ADA3227, ADA5922, ADA5950, ADA6752, ADA7130, ADA8212, ADA2984, ADA2999, ADA3220, ADA3228, ADA3235, ADA3240, ADA3211, ADA3221, ADA5220, and ADA7158 from HW Sand Corp., DLS 381B, DLS 381C, DLS 382A, DLS 386A, DLS 404A, DLS 405A, DLS 405C, and DLS 403A from Crysta-Lyn Chemical Company, or the like may be used.

In this embodiment, as the dye (U1), one kind selected from a plurality of chemical compounds having light absorbing properties as the dye (U1) may be used solely or two or more kinds thereof may be used in combination.

The dye (U) preferably contains one kind or two or more kinds of dyes (U1). Note that the dye (U) may contain any ultraviolet absorbing dye other than the dye (U1) as necessary in the range not impairing the effects of the dye (U1).

The content of the dye (U) in the absorption layer is preferably determined so that the absorption layer has a wavelength at which transmittance becomes 50% at a wavelength of 400 to 425 nm of the spectral transmittance curve at an incident angle of 0° of the present filter. The dye (U) is preferably contained by 0.01 to 30 mass % relative to the mass of the transparent resin in the absorption layer, more preferably 0.05 to 25 mass %, even more preferably 0.1 to 20 mass %.

(Transparent Resin (B))

The transparent resin (B) preferably has a refractive index of 1.45 or more. The refractive index is more preferably 1.5 or more, particularly preferably 1.6 or more. The refractive index of the transparent resin (B) has no particular upper limit, but is preferably about 1.72 for availability or the like. The refractive index as used herein means a refractive index at a wavelength of 589 nm at 20° C. unless particularly described otherwise.

Examples of the transparent resin (B) include an acrylic resin, an epoxy resin, an ene-thiol resin, a polycarbonate resin, a polyether resin, a polyarylate resin, a polysulfone resin, a polyethersulfone resin, a polyparaphenylene resin, a polyarylene ether phosphine oxide resin, a polyimide resin, a polyamide-imide resin, a polyolefin resin, a cyclic olefin resin, and a polyester resin. As the transparent resin (B), one kind may be selected and used solely from these resins, or two or more kinds may be mixed and used.

From the above resins, from the viewpoint of solubility of the dye (A) or the dye (U) to the transparent resin (B), the transparent resin is preferably one or more kinds selected from an acrylic resin, a polyester resin, a polycarbonate resin, an ene-thiol resin, an epoxy resin, a polyimide resin, and a cyclic olefin resin. The transparent resin is more preferably one or more kinds selected from an acrylic resin, a polyester resin, a polycarbonate resin, a polyimide resin, and a cyclic olefin resin. The polyester resin is preferably a polyethylene terephthalate resin, a polyethylene naphthalate resin, and the like.

The refractive index of the transparent resin (B) can be adjusted in the above range by, for example, adjusting a molecule structure of raw material components so as to have a specific structure in a main chain or side chains of a polymer. One example of a structure to have in the polymer so as to adjust the refractive index in the above range is a fluorene skeleton expressed by following formulae (B1) and (B2).

[Chemical 23]

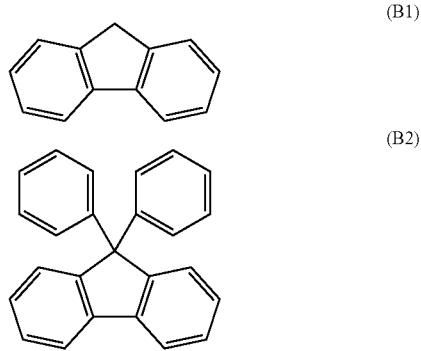

(B1)

(B2)

As the transparent resin (B), a commercial product may be used. One commercial product of the acrylic resin is a resin obtained by curing OGSOL (registered trademark) EA-F5003 (product name, manufactured by Osaka Gas Chemicals Co., Ltd., refractive index: 1.59). Further, one example of an acrylic resin already available as a polymer is a polymethyl methacrylate (refractive index: 1.49) and a polyisobutyl methacrylate (refractive index: 1.48) manufactured by Tokyo Chemical Industry Co., Ltd.

Further, the glass transition temperature (Tg) of the transparent resin is preferably from 0 to 380° C., more preferably from 40 to 370° C., further preferably from 100 to 360° C., even more preferably from 200 to 360° C. When Tg of the transparent resin is in the above range, deterioration or deformation by heat can be suppressed. Among them, a resin with high Tg can suppress heat agitation of the dye, and can suppress heat expansion of the resin itself. Thus, when the dielectric multilayer film is provided in the resin (absorption layer), appearance defects due to occurrence of a crack or the like can be reduced. One example of the resin with Tg of 100 to 360° C. is a polyester resin or the like in which the above-described fluorene skeleton is introduced. Examples of the resin with Tg of 200 to 360° C. include a polyimide resin, a polyethersulfone resin, a polyallyl ether resin, or the like.

Further, examples of commercial products of the polyester resin include OKPH4HT (refractive index: 1.64), OKPH4 (refractive index: 1.61), B-OKP2 (refractive index: 1.63), and OKP850 (refractive index: 1.64) manufactured by Osaka Gas Chemicals Co., Ltd., and Vylon (registered trademark) 103 (refractive index: 1.58) manufactured by Toyobo Co., Ltd. Examples of commercial products of the polycarbonate resin include SP3810 (manufactured by Teijin Chemicals Ltd., refractive index: 1.64), and LeXan (registered trademark) ML9103 (manufactured by Sabic, refractive index: 1.59). Examples of polymer alloys include Panlite (registered trademark) AM-8 series (manufactured by Teijin Chemicals Ltd.), which is an alloy of polycarbonate and polyester, and xylex (registered trademark) 7507 (manufactured by Sabic). Examples of polyimide resins include C3630 (refractive index: 1.59) and C3450 (refractive index: 1.62) manufactured by Mitsubishi Gas Chemical Company, Inc.

(Other Components)

The absorption layer may further contain, within the range not impairing the effects of the present invention, various optional components which this type of absorption layer typically contains, besides the above-described dye (A) and dye (U). Examples of the optional components include a color tone correcting dye, a leveling agent, an antistatic agent, a heat stabilizer, a light stabilizer, an antioxidant, a dispersing agent, a flame retardant, a lubricant and a plasticizer.

(Absorption Layer)

The absorption layer can be formed by, for example, preparing a coating liquid by dissolving or dispersing the dye (A), the dye (U), and the transparent resin (B) or raw material components of the transparent resin (B), as well as components blended as necessary in a solvent, applying this on the transparent substrate and drying it, and moreover curing it as necessary.

The solvent for dissolving or dispersing the dye (A), the dye (U), the transparent resin (B), and the like is not particularly limited as long as it is a dispersion medium in which their raw material components and components blended as necessary can be dispersed or dissolved stably. Note that the term "solvent" as used herein has a concept which includes both the dispersion medium and the solvent. Examples of the solvent include alcohols such as diacetone alcohol, ethyl cellosolve, methyl cellosolve, tridecyl alcohol, cyclohexyl alcohol, and 2-methylcyclohexyl alcohol, glycols such as ethylene glycol, diethylene glycol, triethylene glycol, propylene glycol, dipropylene alcohol, and glycerin, ketones such as acetone, methyl ethyl ketone, methyl isobutyl ketone, cyclopentanone, cyclohexanone, isophorone, and diacetone alcohol, amides such as 1-methyl-2-pyrrolidone, N,N-dimethylformamide, N,N-dimethylacetamide, sulfoxides, ethers, and esters, aliphatic halogenated hydrocarbons such as chloroforms, methylene chloride, dichloroethylene, carbon tetrachloride, and trichloroethylene, aromatic series, aliphatic hydrocarbons, and fluorine-based solvent. One kind may be selected and used solely from these solvents, or two or more kinds may be mixed and used.

The concentration when the transparent resin (B) or the raw material components of the transparent resin (B) are dissolved in the solvent is preferably 2 to 50 mass %, more preferably 5 to 40 mass % relative to the entire coating liquid.

The coating liquid can contain a surface active agent. By containing the surface active agent, an appearance, particularly voids due to minute bubbles, dents due to adherence of foreign objects, crawling in a drying process, can be improved. The surface active agent is not particularly limited, and cation-based, anion-based, or nonionic-based agents and the like can be optionally used.

The solid concentration of the transparent resin (B), the dye (A), the dye (U), and the like in the coating liquid is generally 10 to 60 mass %. When the solid concentration is too low, coating unevenness can easily occur. Conversely, when the solid concentration is too high, a defect of coating appearance can easily occur.

To apply the coating liquid, for example, a coating method such as an immersion coating method, a cast coating method, a spray coating method, a spinner coating method, a bead coating method, a wire bar coating method, a blade coating method, a roller coating method, a curtain coating method, a slit die coater method, a gravure coater method, a slit reverse coater method, a microgravure method, an ink-jet method, or a comma coater method can be used. Besides them, a bar coater method, a screen printing method, a flexographic printing method, or the like can be used.

After the coating liquid is applied on the transparent substrate, it is dried to form the absorption layer. For the drying, heat drying, hot-air drying, or the like can be used. When the coating liquid contains raw material components of the transparent resin, a curing treatment is further performed. When the reaction is thermosetting, it is possible to simultaneously carry out drying and curing, but when it is photosetting, the curing treatment is provided separately from drying.

Note that the absorption layer formed by applying the coating liquid on a releasable support substrate other than the transparent substrate can be removed from the support substrate and adhered on the transparent substrate. The shape and the material of releasable support substrate are not particularly limited as long as it has releasability. Specifically, a glass plate, or a plastic film subjected to a releasing treatment, for example, a film constituted of polyester resin such as polyethylene terephthalate or polybutylene terephthalate, polyolefin resin such as polyethylene, polypropylene, or ethylene-vinyl acetate copolymer, acrylic resin such as polyacrylate, or polymethyl methacrylate, urethane resin, vinyl chloride resin, fluorocarbon resin, polycarbonate resin, polyvinyl butyral resin, polyvinyl alcohol resin, or the like, a stainless steel, or the like is used.

Further, the absorption layer can be produced in a film shape by extrusion molding depending on the type of the transparent resin, and moreover, a plurality of produced films may be stacked and integrated by thermocompression, or the like. They are thereafter adhered on the transparent substrate.

Note that upon application of the coating liquid, the transparent substrate (or releasable substrate) may be subjected to a pretreatment. Aminosilanes, epoxysilanes, vinyl sinales, γ-methacryloxypropyl trimethoxy silane, γ-chloropropyl trimethoxy silane, γ-mercaptopropyl trimethoxysilane, (3-ureidopropyl)trimethoxysilane, and the like can be used as a pretreatment agent. One kind of them can be used solely, or two or more kinds of them can be mixed and used.

It is preferred that the absorption layer satisfies following requirements (4), (5), (6). Further, it is more preferred that the absorption layer satisfies following requirements (4), (5)', (6).

(4) The absorption layer has a maximum absorption wavelength in the wavelength range of 650 to 900 nm, preferably 650 to 750 nm, more preferably 680 to 720 nm in an absorption spectrum of a wavelength range of 500 to 900 nm.

(5) The absorption layer has at least two wavelengths at which the transmittance becomes 10% in the wavelength range of 600 to 800 nm in the spectral transmittance curve at an incident angle of 0°, and a difference IR10(L)-IR10(S) between the longest wavelength IR10(L) and the shortest wavelength IR10(S) of the wavelengths at which the transmittance becomes 10% is 30 to 70 nm. The difference is preferably 35 to 70 nm, more preferably 35 to 65 nm.

When the difference is less than 30 nm, by a change in the spectral transmittance curve due to the incident angle by the reflection layer, a change in the spectral transmittance curve due to the incident angle may also occur in the present filter. On the other hand, when the difference exceeds 70 nm, the absorption spectrum becomes broad, the spectral transmittance curve of the present filter largely displaces from the relative visibility curve, and it is possible that color reproducibility of redness cannot be obtained with high accuracy.

(5)' The absorption layer has at least two wavelengths at which the transmittance becomes 1% in the wavelength range of 600 to 800 nm in the spectral transmittance curve at an incident angle of 0°, and a difference IR1(L)-IR1(S) is 25 to 50 nm between the longest wavelength IR1(L) and the shortest wavelength IR1(S) of the wavelengths at which the transmittance becomes 1%. The difference is preferably 30 to 45 nm, more preferably 33 to 40 nm.

When the difference is less than 25 nm, by a change in the spectral transmittance curve due to the incident angle by the reflection layer, a change in the spectral transmittance curve due to the incident angle may also occur in the present filter. On the other hand, when the difference exceeds 50 nm, the absorption spectrum becomes broad, the spectral transmittance curve of the present filter largely displaces from the relative visibility curve, and color reproducibility of redness cannot be obtained with high accuracy.

(6) Ratio $T_{(620-700)}/T_{(495-570)}$ of average transmittance $T_{(620-700)}$ of light in the wavelength range of 620 to 700 nm and average transmittance $T_{(495-570)}$ of light in the wavelength range of 495 to 570 nm is 0.35 or less in the spectral transmittance curve at an incident angle of 0° The ratio $T_{(620-700)}/T_{(495-570)}$ is preferably 0.30 or less, more preferably 0.28 or less. When the absorption layer satisfies the requirements (4), (5), (6), the present filter can easily obtain a spectral characteristic satisfying the requirements (1) to (3).

Further, when the absorption layer satisfies the requirements (4), (5), (6), providing the absorption layer on an absorption-type glass containing CuO, a high light absorption property in the near-infrared wavelength range can be obtained as an optical filter. The optical filter using the absorption-type glass is more preferred to include an absorption layer satisfying the requirements (4), (5)', (6).

[Reflection Layer]

The reflection layer is often constituted of a dielectric multilayer film made by alternately stacking a dielectric film with a low refractive index (low dielectric film) and a dielectric film with a high refractive index (high dielectric film). Here, the low-refractive index and the high-refractive index mean to have a low refractive index and a high refractive index with respect to the refractive index of an adjacent layer. The high dielectric film preferably has a refractive index of 1.6 or more, more preferably 2.2 to 2.5. Examples of high dielectric film materials include $Ta_2O_5$, $TiO_2$, and $Nb_2O_5$. Among them, $TiO_2$ is preferred from the points of reproducibility, stability, and the like with respect to film formability, refractive index, and the like. On the other hand, the low dielectric film preferably has a refractive index which is less than 1.6, more preferably 1.45 or more and less than 1.55, even more preferably 1.45 to 1.47. Examples of low dielectric film materials include $SiO_2$ and SiO$_x$N$_y$. SiO$_2$ is preferred from the points of reproducibility, stability, economy, and so on in film formability.

The reflection layer exhibits a function to control transmitting and blocking of light in a specific wavelength range by utilizing interference of light, and there is incident angle dependence in its transmitting and blocking property. In general, the wavelength of light blocked by reflection is a shorter wavelength for light incident obliquely than light incident perpendicularly (incident angle of 0°).

In this embodiment, the dielectric multilayer film constituting the reflection layer preferably satisfies the following requirement (7).

(7) Average transmittance in the wavelength range of 420 to 695 nm is 90% or more in the spectral transmittance curve at an incident angle of 0°, and average transmittance in the wavelength range of 750 to 1100 nm is 10% or less. The average transmittance in the wavelength range of 420 to 695 nm is preferably 93% or more, more preferably 95% or more, even more preferably 97% or more. Further, the average transmittance in the wavelength range of 750 to 1100 nm is preferably 7% or less, more preferably 5% or less, even more preferably 3% or less.
When the reflection layer satisfies the requirement (7), the present filter can easily obtain a spectral characteristic satisfying the requirements (1) to (3).

Further, the reflection layer preferably satisfies the following requirement (8).
(8) Average transmittance in the wavelength range of 350 to 400 nm is 10% or less in the spectral transmittance curve at an incident angle of 0°. The average transmittance in the wavelength range of 350 to 400 nm is preferably 7% or less, more preferably 5% or less, even more preferably 3% or less.
When the reflection layer satisfies the requirement (8), a filter having a cutting property with respect to light in an ultraviolet wavelength range can be obtained. Further, the present filter satisfies the requirement (9) when it satisfies the requirement (7).

Moreover, in the reflection layer, preferably, transmittance steeply changes in a boundary wavelength range of a blocking wavelength with a transmitted light wavelength. The dielectric multilayer film constituting the reflection layer for this purpose preferably has, as the total number of stacks of a low-refractive index film and a high-refractive index film, 15 layers or more, more preferably 25 layers or more, even more preferably 30 layers or more. However, when the total number of layers becomes large, warping of the dielectric multilayer film, or the like occurs. Further, the dielectric multilayer film preferably has 100 layers or less, more preferably 75 layers or less, even more preferably 60 layers or less.

The film thickness of the dielectric multilayer film is preferred to be thin from the viewpoint of thinning of the optical filter after satisfying the preferred number of stacks. The film thickness of such a dielectric multilayer film is preferably 2 to 10 μm, though depending on a selected wavelength blocking property.

To form the dielectric multilayer film, for example, a vacuum film-forming process such as CVD method, sputtering method, vacuum deposition method, and the like or a wet film-forming process such as spray method, dip method, and the like can be used.

Note that the reflection layer may have a predetermined reflecting property in a single layer (a group of dielectric films), or may have a predetermined reflecting property in a plurality of layers. When a plurality of layers are provided, for example, they may be provided on one side of the transparent substrate, or on both sides sandwiching the transparent substrate.

As used herein, with respect to transmittance in a specific wavelength range, transmittance of 90% or more for example means that the transmittance does not become lower than 90% in this entire wavelength range, and likewise transmittance of 2% or less for example means that the transmittance does not exceed 2% in this entire wavelength range.

[Anti-Reflection Layer]
Examples of the anti-reflection layer include a dielectric multilayer film, an intermediate refractive index medium, and moth-eye structure having a refractive index which gradually changes. Among others, use of the dielectric multilayer film is preferred in view of optical efficiency and productivity. The dielectric multilayer film used in the anti-reflection layer can be obtained similarly by alternately stacking the low-refractive index film and the high-refractive index film similarly to the dielectric multilayer film used for the reflection layer.

The structure of the present filter is not particularly limited except having the absorption layer and the reflection layer, and any other component can be added. One example of other components is inorganic particles or the like controlling transmission and absorption of light with a specific wavelength range. Specific examples of inorganic particles include ITO (indium Tin Oxides), ATO (Antimony-doped Tin Oxides), cesium tungstate, and lanthanum boride. The ITO particles and the cesium tungstate particles have high transmittance of visible light, and have a wide range of light absorbing property including the infrared wavelength range exceeding 1200 nm. Thus, it is preferred when a blocking property of such an infrared light is needed.

Further, the present filter can be used also by directly adhering via an adhesive layer to a solid-state image sensing device, an imaging lens, or the like of an imaging device.

The NIR filter of the present invention is preferably used in a solid-state imaging device of a digital still camera or the like, and is disposed, for example, between the imaging lens and the solid-state image sensing device.

<Imaging Device>
An example of a solid-state imaging device 20 according to the present invention will be explained below with reference to FIG. 2.
The imaging device 20 of this embodiment has a solid-state image sensing device 21, a near-infrared cut filter 22 according to the present invention, an imaging lens 23, and a case 24 accommodating them. The imaging lens 23 is fixed by a lens unit 25 further provided inside the case 24. The solid-state image sensing device 21 and imaging lens 23 are disposed along an optical axis x. The imaging lens 23 and the solid-state image sensing device 21 are electronic parts converting light which passed through the imaging lens 23 into an electronic signal, and specifically a CCD or a CMOS or the like is used for it.
Then, in an example of the drawings, a near-infrared cut filter illustrated in FIG. 1E is used as the near-infrared cut filter 22, and is disposed so that its reflection layer 12 side is directed toward the solid-state image sensing device 21 side.

In the imaging device 20 structured in this manner, light incident through the imaging lens 23 passes through the near-infrared cut filter 22 and received on the solid-state image sensing device 21, and this received light is converted by the solid-state image sensing device 21 into an electric signal and is outputted as an imaging signal. As the near-infrared cut filter 22, an optical filter having an excellent oblique-incidence property and exhibiting a spectral characteristic is used, which is quite close to the relative visibility curve particularly on the long wavelength side. Thus, the imaging device 20 can obtain a high-quality taken image which excels significantly in color reproducibility.

Figure 2:
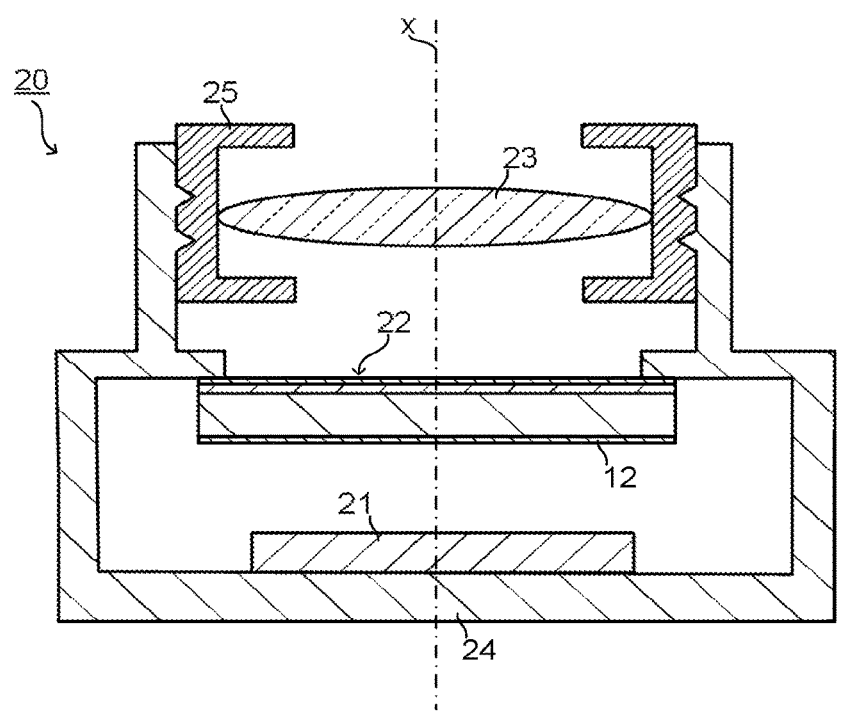
FIG. 2 is a cross-sectional view schematically illustrating an example of an imaging device of one embodiment.

Note that in the imaging device 20 illustrated in FIG. 2, the near-infrared cut filter 22 is disposed between the imaging lens 23 and the solid-state image sensing device 21, but its disposed position is not particularly limited as long as it is in front of the solid-state image sensing device 21. Further, in the imaging device 20, the imaging lens 23 is constituted only of one lens, but may be a combination of a plurality of lenses.

EXAMPLE

Next, the present invention will be more specifically explained by using examples. Examples 1 to 5 and 9 are examples of the present invention, and Examples 6 to 8 are comparative examples.

Example 1

Figure 3:
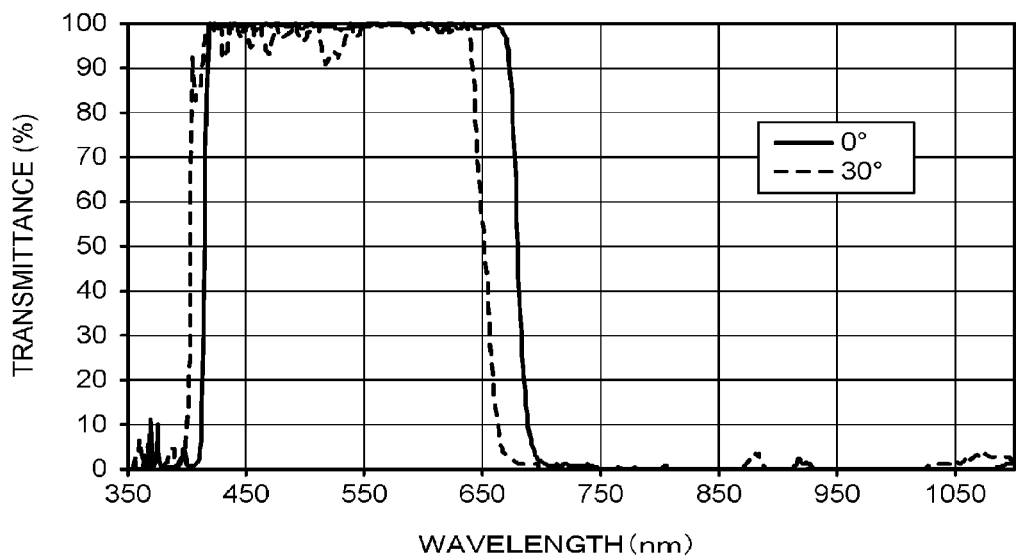
FIG. 3 is a chart illustrating a spectral transmittance curve of a reflection layer used in an NIR filter of an example.

On a glass (none-alkali glass; product name: AN100, manufactured by Asahi Glass Co., Ltd.) substrate having a thickness of 0.3 mm, a $TiO_2$ film as a high-refractive index film and an $SiO_2$ film as a low-refractive index film were stacked alternately by a vapor deposition method, thereby forming a reflection layer constituted of an dielectric multilayer film of 52 layers. The structure of the reflection layer was obtained by performing a simulation with the number of stacks of the dielectric multilayer film, a film thickness of the $TiO_2$ film and a film thickness of the $SiO_2$ film being parameters, so that transmittance with a wavelength of 350 to 400 nm is 10% or less, transmittance with a wavelength of 420 to 695 nm is 90% or more, and transmittance with a wavelength of 750 to 1100 nm is 10% or less in the spectral transmittance curve at an incident angle of 0°. FIG. 3 illustrates a spectral transmittance curve (incident angles of 0° and 30°) of a reflection layer produced based on the above design.

Further, to a cyclohexanone solution having a polyester resin (product name: OKP850; refractive index: 1.64, manufactured by Osaka Gas Chemicals Co., Ltd.) of 18 mass %, 1-[3-(trimethoxysilyl)propyl]urea was added and dissolved as a silane coupling agent by a ratio to be 3 mass % relative to the mass of the polyester resin. Moreover, to this resin solution, the NIR absorbing dye (chemical compound F11-7) was added and dissolved by a ratio to be 9 mass % relative to the mass of the polyester resin, thereby preparing a coating liquid for forming an absorption layer.

This coating liquid was applied by a spin coating method on a surface opposite to a reflection layer formation surface of the glass substrate on which the reflection layer is formed, and then heated under atmospheric pressure for five minutes at 90° C. and then one hour at 150° C., thereby forming an absorption layer with a thickness of 1 μm. Thereafter, the $TiO_2$ film and the $SiO_2$ film were stacked alternately on the surface of the absorption layer by a vapor deposition method so as to form the anti-reflection layer similarly to the reflection layer, thereby obtaining a near-infrared cut filter. Note that the structure of the anti-reflection layer was determined by a simulation with the number of stacks of dielectric multilayer film, a film thickness of the $TiO_2$ film and a film thickness of the $SiO_2$ film being parameters so as to have a predetermined optical property.

Examples 2 to 8

NIR filters were produced similarly to Example 1 while changing the type and/or addition amount of an NIR absorbing dye to be added to the coating liquid for forming the absorption layer as described in Table 3, except that in Example 5 and Example 6 an UV absorbing dye is further added by a ratio described in Table 3 in addition to the NIR absorbing dye.

Example 9

An NIR filter was produced similarly to Example 1 except that the glass substrate was a fluorophosphate glass (product name: NF-50T, 0.25 mm thickness, manufactured by Asahi Glass Co., Ltd.) substrate, and the types and/or addition amounts of a transparent resin, an NIR absorbing dye and a UV absorbing dye used in the coating liquid for forming the absorption layer were set as described in Table 3.

(Spectral Characteristic of the Absorption Layer)

Separately from the production of the above-described NIR filters, the coating liquid for forming an absorption layer prepared in each of the above examples was applied by a spin coating method on a glass substrate, and then heated under an atmospheric pressure for five minutes at 90° C. and then one hour at 150° C., thereby forming an absorption layer with a thickness of 1 μm.

The spectral transmittance curve of each absorption layer formed was measured with the atmospheric air being the background by using an ultraviolet visible spectrophotometer (model name: U4100 manufactured by Hitachi High-Technologies Corporation), and respective spectral characteristics were calculated from measurement results thereof. The results are presented together in Table 3.

(Spectral Characteristic of the NIR Filter)

Figure 4:
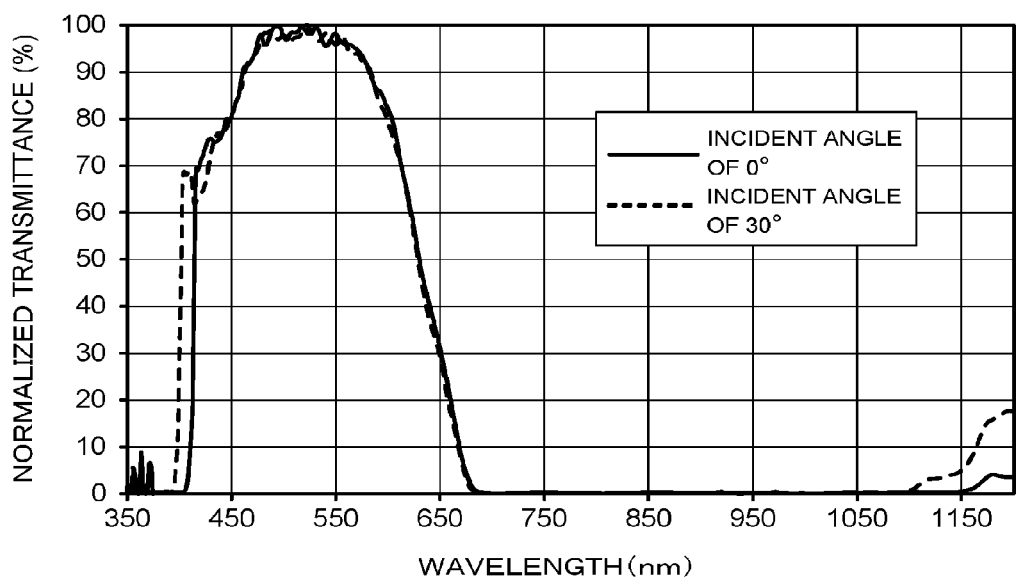
FIG. 4 is a chart illustrating a spectral transmittance curve of the NIR filter obtained in the example.

The spectral transmittance curve (incident angle of 0° and 30°) of the NIR filter obtained in Examples 1 to 9 was measured using the above-described ultraviolet visible spectrophotometer. The obtained spectral transmittance curve was normalized with maximum transmittance in the wavelength range of 450 to 650 nm, and each spectral characteristic was calculated. Results are presented in Table 4. Further, the normalized spectral transmittance curve of Example 4 is illustrated in FIG. 4.

TABLE 3

|  |  |  | Example 1 | Example 2 | Example 3 | Example 4 | Example 5 | Example 6 | Example 7 | Example 8 | Example 9 |
|---|---|---|---|---|---|---|---|---|---|---|---|
| Transparent substrate | Glass substrate | | AN100 | AN100 | AN100 | AN100 | AN100 | AN100 | AN100 | AN100 | NF50T |
| | Thickness (mm) | | 0.3 | 0.3 | 0.3 | 0.3 | 0.3 | 0.3 | 0.3 | 0.3 | 0.25 |
| Absorption layer | Transparent resin | Kind | OKP850 | OKP850 | OKP850 | OKP850 | OKP850 | OKP850 | OKP850 | OKP850 | C3630 |
| | | Refractive index | 1.64 | 1.64 | 1.64 | 1.64 | 1.64 | 1.64 | 1.64 | 1.64 | 1.59 |

TABLE 3-continued

|  |  | Example 1 | Example 2 | Example 3 | Example 4 | Example 5 | Example 6 | Example 7 | Example 8 | Example 9 |
|---|---|---|---|---|---|---|---|---|---|---|
| NIR absorption dye | Abbr. chemical compound | F11-7 | F11-5 | F11-5 | F11-5 | F11-5 | F11-2 | F11-5 | F11-5 | F11-2 |
|  | Addition amount* (mass %) | 9 | 7 | 9 | 10 | 7 | 9 | 5.3 | 25.5 | 4 |
| UV absorbing dye | Abbr. chemical compound | — | — | — | — | M-2 | M-2 | — | — | M-2 |
|  | Addition amount* (mass %) | — | — | — | — | 4.5 | 4.5 | — | — | 3 |
|  | thickness (μm) | 1.0 | 1.0 | 1.0 | 1.0 | 1.0 | 1.0 | 1.0 | 1.0 | 1.0 |
| Spectral transmittance | IR1(L)-IR1(S) (nm) | 33.3 | 32.0 | 39.7 | 44.9 | 35.8 | 32.9 | 18.2 | 69.2 | 0 |
|  | IR10(L)-IR10(S) (nm) | 62.4 | 56.0 | 62.5 | 66.4 | 63.2 | 43.1 | 23.0 | 69.5 | 41.0 |
|  | $T_{(620-700)}/T_{(495-570)}$ | 0.34 | 0.28 | 0.23 | 0.20 | 0.25 | 0.39 | 0.35 | 0.06 | 0.25 |

*Ratio relative to the mass of transparent resin

TABLE 4

|  |  | Example 1 | Example 2 | Example 3 | Example 4 | Example 5 | Example 6 | Example 7 | Example 8 | Example 9 |
|---|---|---|---|---|---|---|---|---|---|---|
| NIR filter | Ave. transmittance (G) of 495-570 nm | 94.6 | 95.6 | 94.3 | 94.2 | 94.1 | 94.7 | 94.7 | 92.1 | 93.2 |
|  | Ave. transmittance (R) of 620-750 nm | 18.5 | 18.7 | 14.8 | 13.4 | 17.0 | 23.4 | 20.9 | 3.5 | 15.6 |
|  | (R)/(G) | 0.19 | 0.19 | 0.16 | 0.14 | 0.18 | 0.25 | 0.22 | 0.04 | 0.17 |
|  | $|T_{0(600-725)}-T_{30(600-725)}|$ (% · nm) | 2.82 | 1.24 | 2.63 | 2.56 | 1.28 | 1.68 | 2.98 | 1.74 | 1.78 |
|  | $\lambda IR_{T(80)}-\lambda_{T(80)}$ (nm) | 19.1 | 19.1 | 14.7 | 12.3 | 19.0 | 28.1 | 21.8 | −12.0 | 1.1 |
|  | $\lambda IR_{T(50)}-\lambda_{T(50)}$ (nm) | 36.8 | 36.8 | 26.9 | 23.4 | 32.8 | 42.5 | 43.0 | 1.3 | 23.5 |
|  | $\lambda IR_{T(20)}-\lambda_{T(20)}$ (nm) | 36.9 | 36.9 | 30.9 | 28.1 | 34.1 | 43.6 | 40.4 | −3.7 | 34.9 |
|  | Ave. transmittance of 750-850 nm | 0.02 | 0.02 | 0.02 | 0.02 | 0.02 | 0.06 | 0.02 | 0.02 | 0.002 |

From Table 3 and Table 4, in the near-infrared cut filter of Examples 1 to 5 and 9, the incident angle dependence is improved, and transmittance in the long wavelength range of the visible wavelength range is quite close to the relative visibility curve. Therefore, spectral sensitivity of the solid-state image sensing device using this near-infrared cut filter becomes quite close to normal visibility of human, and good color reproducibility can be obtained.

On the other hand, in Examples 6, 7, the oblique-incidence property is good but the transmittance of red (R) is high with respect to the transmittance of green (G), and a separation from the relative visibility curve is large and good color reproducibility cannot be obtained. In Example 8, the oblique-incidence property is good, and the transmittance (R)/(G) of red with respect to green is suppressed. However, the wavelength $\lambda IR_{T(80)}$ at which transmittance exhibits 80% and the wavelength $\lambda IR_{T(20)}$ at which transmittance exhibits 20% (wavelength $\lambda_{T(80)}$ and wavelength $\lambda_{T(20)}$, respectively) are on the short wavelength side with respect to the relative visibility curve, and good color reproducibility cannot be obtained.

(Heat Resistance)

In order to evaluate heat resistance, a glass substrate with an absorption layer was prepared, having an absorption layer containing a squarylium-based compound of the formulae (F11-7), (F11-5), and (F11-2) in a polyester resin (OKP850) and a polyimide resin (C3630) on a glass substrate (AN100) The glass substrate with the absorption layer was heated for 3 hours at 160° C., an absorption constant at the maximum absorption wavelength of the contained dye was measured, and a dye residual rate (%) was calculated with a following equation. Results are presented in Table 5.

Dye residual rate (%)=(absorption constant at maximum absorption wavelength after heating)/(absorption constant at initial maximum absorption wavelength)×100

TABLE 5

| Transparent resin | Kind | OKP850 | OKP850 | OKP850 | C3630 | C3630 | C3630 |
|---|---|---|---|---|---|---|---|
|  | Tg (° C.) | 150 | 150 | 150 | 320 | 320 | 320 |
| NIR absorption dye | Abbr. chemical compound | F11-7 | F11-5 | F11-2 | F11-7 | F11-5 | F11-2 |
| Dye residual rate [160° C., 3 hrs] |  | 92% | 89% | 92% | 98% | 97% | 98% |

From Table 5, the glass substrate with the absorption layer having the absorption layer containing the squarylium-based compound in a polyester resin or a polyimide resin has a high dye residual rate after heated for three hours at 160° C. Therefore, the NIR filter of the examples can retain the initial spectral transmittance even after undergoing a heating process, that is, can obtain the effect of suppressing a change in spectral transmittance.

The near-infrared cut filter according to the present invention has low incident angle dependence and moreover has a spectral characteristic quite close to normal visibility of human, and is useful for an imaging device or the like required to have high color reproducibility.

What is claimed is:

1. A near-infrared cut filter, comprising:
   an absorption layer and
   a reflection layer,
   wherein the near-infrared cut filter satisfies following requirements (1) and (3):
   (1) average transmittance (R) in the wavelength range of 620 to 750 nm is 20% or less and average transmittance (G) in the wavelength range of 495 to 570 nm is 90% or more in a spectral transmittance curve at an incident angle of 0°, and the ratio (R)/(G) of the average transmittance is 0.20 or less;
   and
   (3) the near-infrared cut filter has a wavelength $\lambda IR_{T(80)}$ at which transmittance becomes 80%, and a wavelength $\lambda IR_{T(50)}$ at which transmittance becomes 50% in the wavelength range of 550 to 750 nm in the spectral transmittance curve at an incident angle of 0° normalized by maximum transmittance in the wavelength range of 450 to 650 nm, and the wavelengths $\lambda IR_{T(80)}$, and $\lambda IR_{T(50)}$ satisfy following formulae (a) and (b), respectively:

$$0 \leq \lambda IR_{T(80)} - \lambda_{T(80)} \leq 30 \text{ nm} \quad (a),$$

$$0 \leq \lambda IR_{T(50)} - \lambda_{T(50)} \leq 35 \text{ nm} \quad (b),$$

where $\lambda_{T(80)}$ and $\lambda_{T(50)}$ and are wavelengths on a long wavelength side where relative visibility of 0.8 and 0.5 and is exhibited in a relative visibility curve, respectively.

2. The near-infrared cut filter according to claim 1, wherein the absorption layer satisfies following requirements (4) to (6):
   (4) the absorption layer has a maximum absorption wavelength in the wavelength range of 650 to 900 nm in an absorption spectrum in the wavelength range of 500 to 900 nm;
   (5) the absorption layer has at least two wavelengths at which the transmittance becomes 10% in the wavelength range of 600 to 800 nm in the spectral transmittance curve at an incident angle of 0°, and a difference IR10(L)–IR10(S) between the longest wavelength IR10(L) and the shortest wavelength IR10(S) of the wavelengths at which the transmittance becomes 10% is 30 to 70 nm; and
   (6) ratio $T_{(620-700)}/T_{(495-570)}$ of average transmittance $T_{(620-700)}$ in the wavelength range of 620 to 700 nm to average transmittance $T_{(495-570)}$ in the wavelength range of 495 to 570 nm is 0.35 or less, in the spectral transmittance curve at an incident angle of 0°.

3. The near-infrared cut filter according to claim 2, wherein the absorption layer further satisfies a following requirement (5)':
   (5)' the absorption layer has at least two wavelengths at which the transmittance becomes 1% in the wavelength range of 600 to 800 nm in the spectral transmittance curve at an incident angle of 0°, and a difference IR1(L)–IR1(S) between the longest wavelength IR1(L) and the shortest wavelength IR1(S) of the wavelengths at which the transmittance becomes 1% is 25 to 50 nm.

4. The near-infrared cut filter according to claim 1, wherein the reflection layer satisfies a following requirement (7):
   (7) in the spectral transmittance curve at an incident angle of 0°, average transmittance in the wavelength range of 420 to 695 nm is 90% or more, and average transmittance in the wavelength range of 750 to 1100 nm is 10% or less.

5. The near-infrared cut filter according to claim 1, wherein the reflection layer further satisfies a following requirement (8):
   (8) average transmittance in the wavelength range of 350 to 400 nm is 10% or less in the spectral transmittance curve at an incident angle of 0°.

6. The near-infrared cut filter according to claim 1, wherein the reflection layer further satisfies a following requirement (9):
   (9) average transmittance in the wavelength range of 750 to 850 nm is 0.2% or less in the spectral transmittance curve at an incident angle of 0°.

7. The near-infrared cut filter according to claim 1, further comprising a transparent substrate, wherein the absorption layer and the reflection layer are disposed on a main surface of the transparent substrate.

8. The near-infrared cut filter according to claim 7, wherein the absorption layer is disposed on a main surface of the transparent substrate, and the reflection layer is disposed on the other main surface of the transparent substrate.

9. The near-infrared cut filter according to claim 8, further comprising an antireflection layer disposed on the absorption layer.

10. The near-infrared cut filter according to claim 8, wherein the reflection layer is disposed on the absorption layer.

11. The near-infrared cut filter according to claim 7, wherein both the absorption layer and the reflection layer are disposed on each of the main surfaces.

12. The near-infrared cut filter according to claim 7, wherein the transparent substrate comprises a resin or a glass.

13. The near-infrared cut filter according to claim 12, wherein the transparent substrate comprises an absorption-type glass.

14. The near-infrared cut filter according to claim 1, wherein the absorption layer comprises at least one near-infrared absorbing material selected from the group consisting of a cyanine-based compound, a phthalocyanine-based compound, a naphthalocyanine-based compound, a dithiol metal complex-based compound, a diimonium-based compound, a polymethine-based compound, a phthalide compound, a naphthoquinone-based compound, an anthraquinone-based compound, an indophenol-based compound, and a squarylium-based compound.

15. The near-infrared cut filter according to claim 14, wherein the absorption layer comprises a chemical compound of formula (F1):

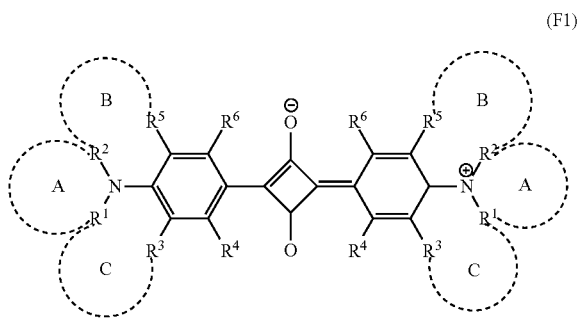

(F1)

in which
- $R^4$ and $R^6$ each independently represent a hydrogen atom, a halogen atom, a hydroxyl group, a $C_1$-$C_6$ alkyl or alkoxy group, a $C_1$-$C_{10}$ acyloxy group, or —$NR^7R^8$ where $R^7$ and $R^8$ each independently represent a hydrogen atom, a $C_1$-$C_{20}$ alkyl group, or —C(=O)—$R^9$, where $R^9$ is a hydrogen atom, an optionally substituted $C_1$-$C_{20}$ alkyl or $C_6$-$C_{11}$ aryl group, or an optionally substituted $C_7$-$C_{18}$ alaryl group which optionally has an oxygen atom between carbon atoms,
- at least one of $R^1$ and $R^2$, $R^2$ and $R^5$, and $R^1$ and $R^3$ optionally forms 5- or 6-membered heterocycles A, B, and C together with a nitrogen atom,
- $R^1$ and $R^2$, when the heterocycle is not formed, each independently represent a hydrogen atom, an optionally substituted $C_1$-$C_6$ alkyl or allyl group, or a $C_6$-$C_{11}$ aryl or alaryl group, and
- $R^3$ and $R^5$, when the heterocycle are not formed, each independently represent a hydrogen atom, a halogen atom, or a $C_1$-$C_6$ alkyl or alkoxy group.

16. The near-infrared cut filter according to claim 14, wherein the absorption layer comprises a chemical compound of formula (F5):

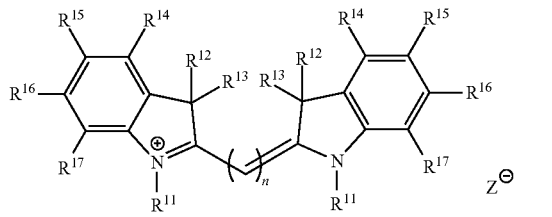

(F5)

in which
- $R^{11}$ each independently represent a $C_1$-$C_{20}$ alkyl, alkoxy or alkyl sulfone group, or an anion species thereof,
- $R^{12}$ and $R^{13}$ each independently represent a hydrogen atom or a $C_1$-$C_{20}$ alkyl group,
- Z represents a $PF_6$, $ClO_4$, $R^f$—$SO_2$, ($R^f$—$SO_2$)$_2$—N, where $R^f$ represents a $C_1$-$C_8$ alkyl group in which at least one hydrogen atom is substituted by a fluorine atom, or $BF_4$,
- $R^{14}$, $R^{15}$, $R^{16}$ and $R^{17}$ each independently represent a hydrogen atom, a halogen atom, or a $C_1$-$C_6$ alkyl group, and
- n represents an integer of 1 to 6.

17. The near-infrared cut filter according to claim 14, wherein the absorption layer comprises an transparent resin, and the at least one near-infrared absorbing material is contained by 0.01 to 30 mass % relative to the mass of the transparent resin in the absorption layer.

18. The near-infrared cut filter according to claim 1, wherein the absorption layer comprises an ultraviolet absorbing material.

19. The near-infrared cut filter according to claim 1, wherein the absorption layer comprises an ultraviolet absorption layer comprising the ultraviolet absorbing material.

20. The near-infrared cut filter according to claim 18, wherein the absorption layer comprises an transparent resin, and the ultraviolet absorbing material is contained by 0.01 to 30 mass % relative to the mass of the transparent resin in the absorption layer.

21. The near-infrared cut filter according to claim 18, wherein the ultraviolet absorbing material comprises a chemical compound of formula (M):

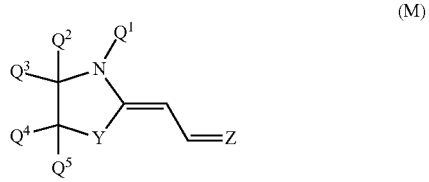

(M)

in which
- Y represents an oxygen atom a methylene group substituted by $Q^6$ and $Q^7$ where $Q^6$ and $Q^7$ each independently represent a hydrogen atom, a halogen atom, or a $C_1$-$C_{10}$ alkyl or alkoxy group;
- $Q^1$ represents an optionally substituted monovalent hydrocarbon group with 1 to 12 carbon atoms;
- $Q^2$ to $Q^5$ each independently represent a hydrogen atom, a halogen atom, or an $C_1$-$C_{10}$ alkyl or alkoxy group; and
- Z represents any of bivalent groups of formulae (Z1) to (Z5):

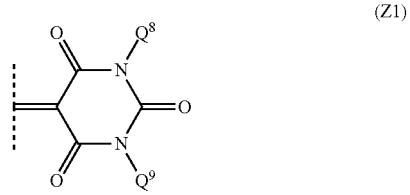

(Z1)

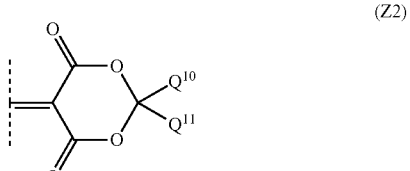

(Z2)

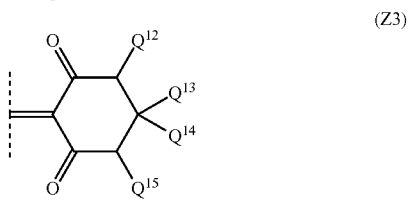

(Z3)

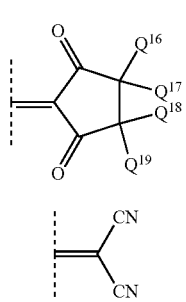 (Z4)

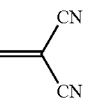 (Z5)

where $Q^8$ and $Q^9$ each independently represent an optionally substituted monovalent hydrocarbon group with 1 to 12 carbon atoms, and $Q^{10}$ to $Q^{19}$ each independently represent a hydrogen atom or an optionally substituted monovalent hydrocarbon group with 1 to 12 carbon atoms.

22. The near-infrared cut filter according to claim 18, wherein the absorption layer has a maximum absorption wavelength in the wavelength range of 360 to 415 nm in an absorption spectrum in the wavelength range of 350 to 800 nm.

23. An imaging device comprising the near-infrared cut filter according to claim 1.

24. The near-infrared cut filter according to claim 1, wherein the near-infrared cut filter has a wavelength $\lambda IR_{T(20)}$ at which transmittance becomes 20% in the wavelength range of 550 to 750 nm in the spectral transmittance curve at an incident angle of 0° normalized by maximum transmittance in the wavelength range of 450 to 650 nm, and the wavelengths $\lambda IR_{T(20)}$ satisfy following formula (c):

$$0 \leq \lambda IR_{T(20)} - \lambda_{T(20)} \leq 37 \text{ nm} \quad (c),$$

where $\lambda_{T(20)}$ are wavelengths on a long wavelength side where relative visibility of 0.2 is exhibited in a relative visibility curve.

25. The near-infrared cut filter according to claim 1, wherein the near-infrared cut filter satisfies following requirement (2):

(2) difference $|T_{0(600-725)} - T_{30(600-725)}|$ between an integral value $T_{0(600-725)}$ of transmittance in the wavelength range of 600 to 725 nm in the spectral transmittance curve at an incident angle of 0°, and an integral value $T_{30(600-725)}$ of transmittance in the wavelength range of 600 to 725 nm in a spectral transmittance curve at an incident angle of 30° is 3%-nm or less.

26. The near-infrared cut filter according to claim 24, wherein the wavelengths $\lambda IR_{T(80)}$, $\lambda IR_{T(50)}$, and $\lambda IR_{T(20)}$ further satisfy following formulae (d) and (e):

$$(\lambda IR_{T(80)} - \lambda_{T(80)})/(\lambda IR_{T(50)} - \lambda_{T(50)}) \leq 1.5 \quad (d),$$

$$(\lambda IR_{T(20)} - \lambda_{T(20)})/(\lambda IR_{T(50)} - \lambda_{T(50)}) \leq 2.0 \quad (e).$$

* * * * *